(12) United States Patent
Marui et al.

(10) Patent No.: US 8,765,469 B2
(45) Date of Patent: Jul. 1, 2014

(54) METHOD OF PRODUCING LYMPHOCYTES

(75) Inventors: Takahiro Marui, Otsu (JP); Kinuko Nagamine, Otsu (JP); Nobuko Muraki, Otsu (JP); Akiko Kato, Otsu (JP); Tatsuji Enoki, Otsu (JP); Hiroaki Sagawa, Otsu (JP); Ikunoshin Kato, Otsu (JP)

(73) Assignee: Takara Bio Inc., Otsu-Shi (JP)

( * ) Notice: Subject to any disclaimer, the term of this patent is extended or adjusted under 35 U.S.C. 154(b) by 434 days.

(21) Appl. No.: 11/990,443

(22) PCT Filed: Aug. 10, 2006

(86) PCT No.: PCT/JP2006/315881
§ 371 (c)(1),
(2), (4) Date: Feb. 14, 2008

(87) PCT Pub. No.: WO2007/020880
PCT Pub. Date: Feb. 22, 2007

(65) Prior Publication Data
US 2010/0150886 A1      Jun. 17, 2010

(30) Foreign Application Priority Data

Aug. 17, 2005   (JP) .................. 2005-236723

(51) Int. Cl.
*C12N 5/00* (2006.01)
*G01N 33/547* (2006.01)
*A61K 35/14* (2006.01)

(52) U.S. Cl.
CPC ............. *A61K 35/17* (2013.01); *C12N 2533/52* (2013.01); *G01N 33/547* (2013.01)
USPC ........... 435/375; 435/325; 435/395; 435/402; 436/531; 436/532

(58) Field of Classification Search
CPC ............................ A61K 35/17; C12N 2533/52
USPC ............................................... 435/325, 375
See application file for complete search history.

(56) References Cited

U.S. PATENT DOCUMENTS

| | | | |
|---|---|---|---|
| 5,102,988 A | 4/1992 | Kimizuka et al. |
| 5,198,423 A | 3/1993 | Taguchi et al. |
| 5,354,686 A | 10/1994 | Haberman |
| 5,827,642 A | 10/1998 | Riddell et al. |
| 5,866,115 A | 2/1999 | Kanz et al. |
| 6,287,864 B1 | 9/2001 | Bagnis et al. |
| 6,316,257 B1 | 11/2001 | Flyer et al. |
| 6,472,204 B2 | 10/2002 | Asada et al. |
| 6,692,964 B1 | 2/2004 | June et al. |
| 6,734,014 B1 | 5/2004 | Hwu et al. |
| 6,821,778 B1 | 11/2004 | Engleman et al. |
| 7,067,318 B2 | 6/2006 | June et al. |
| 7,172,869 B2 | 2/2007 | June et al. |
| 2002/0119568 A1 | 8/2002 | Berenson et al. |
| 2003/0022210 A1 | 1/2003 | Bonyhadi et al. |
| 2004/0101519 A1 | 5/2004 | June et al. |
| 2004/0115809 A1 | 6/2004 | Sagawa et al. |
| 2005/0042208 A1 | 2/2005 | Sagawa et al. |
| 2005/0227354 A1 | 10/2005 | Sagawa et al. |
| 2006/0166924 A1 | 7/2006 | Kato et al. |
| 2006/0246587 A1 | 11/2006 | June et al. |
| 2008/0227204 A1 | 9/2008 | Sagawa et al. |

FOREIGN PATENT DOCUMENTS

| | | |
|---|---|---|
| EP | 0207751 A1 | 1/1987 |
| EP | 0 409 655 A2 | 1/1991 |
| EP | 0523948 A2 | 1/1993 |
| EP | 0795606 A1 | 9/1997 |
| EP | 0 870 839 A1 | 10/1998 |
| EP | 1424387 A1 | 6/2004 |
| EP | 1496109 A1 | 1/2005 |
| EP | 1 666 589 A1 | 6/2006 |
| JP | 3-80076 A | 4/1991 |
| JP | 3284700 A2 | 12/1991 |
| JP | 4-297494 A | 10/1992 |
| JP | 5271291 A2 | 10/1993 |
| JP | 6-172203 A | 6/1994 |
| JP | 6-306096 A | 11/1994 |
| JP | 9-25299 A | 1/1997 |
| JP | 10-29952 A | 2/1998 |
| JP | 2729712 B2 | 3/1998 |
| JP | 11-505419 A | 5/1999 |
| JP | 3104178 B2 | 10/2000 |
| JP | 2001-314183 A | 11/2001 |
| JP | 2003-80817 A | 3/2003 |
| JP | 2004-500095 A | 1/2004 |
| WO | WO 88/02774 A1 | 4/1988 |
| WO | WO 89/01942 A1 | 3/1989 |
| WO | WO 95/84878 A1 | 2/1995 |
| WO | WO 95/11963 A1 | 5/1995 |
| WO | WO 95/28479 A1 | 10/1995 |
| WO | WO 96/00782 A1 | 1/1996 |
| WO | WO-96/06929 A2 | 3/1996 |
| WO | WO 96/16674 A1 | 6/1996 |
| WO | WO 97/01194 A1 | 1/1997 |
| WO | WO 97/05239 A1 | 2/1997 |
| WO | WO 97/11604 A1 | 4/1997 |
| WO | WO 97/11694 A1 | 4/1997 |
| WO | WO-97/18318 A1 | 5/1997 |
| WO | WO-97/32970 A1 | 9/1997 |

(Continued)

OTHER PUBLICATIONS

Lamers et al. Cancer Gene Ther 2002;9:613-23.*

(Continued)

*Primary Examiner* — Janice Li
(74) *Attorney, Agent, or Firm* — Birch, Stewart, Kolasch & Birch, LLP

(57) ABSTRACT

A method for preparing lymphocytes characterized in that the method comprises the step of carrying out expansion in the presence of (a) fibronectin, a fragment thereof or a mixture thereof, (b) a CD3 ligand, and (c) a CD28 ligand.

13 Claims, 1 Drawing Sheet

(56) References Cited

FOREIGN PATENT DOCUMENTS

| WO | WO 98/12306 A1 | 3/1998 |
|---|---|---|
| WO | WO 98/33888 A1 | 8/1998 |
| WO | WO 98/13653 A1 | 11/1998 |
| WO | WO 99/05301 A1 | 2/1999 |
| WO | WO 99/33863 A1 | 7/1999 |
| WO | WO 99/33869 A2 | 7/1999 |
| WO | WO-00/09168 A1 | 2/2000 |
| WO | WO 00/56368 A1 | 9/2000 |
| WO | WO-01/62895 A2 | 8/2001 |
| WO | WO-02/14481 A1 | 2/2002 |
| WO | WO-03/016511 A1 | 2/2003 |
| WO | WO-03/080817 A1 | 10/2003 |
| WO | WO 2004/018667 A1 | 3/2004 |
| WO | WO-2005/019450 A1 | 3/2005 |

OTHER PUBLICATIONS

Rao et al. J Immunol 2000;165:4935-40.*
Sturm et al. J Immunol 2004;173:3889-3900.*
Kim Young-June et al., "4-1BB Costimulation Promotes Human T Cell Adhesion to Fibronectin"; Cellular Immunology 192, 13-23 (1999); XP002544135; ISSN: 0008-8749.
Supplementary European Search Report issued by the EPO in corresponding European Application No. 06782667.7 on Sep. 16, 2009.
Takayama, Tadatoshi et al. Adoptive Immunotherapy to lower postsurgical recurrence rates of hepatocellular carcinoma: a randomised trial, The Lancet, vol. 356, Sep. 2, 2000, pp. 802-807.
Whiteside, Theresa L., Isolation of Human NK Cells and Generation of LAK Activity, Current Protocols in Immunology, 1996, Supp 17, Unit 7.7, pp. 7.7.1-7.7.11.
Zhou, Xu-Yu et al., Molecular Mechanisms Underlying Differential Contribution of CD28 Versus Non-CD28 Costimulatory Molecules to IL-2 Promoter Activation, The Journal of Immunology, 2002, pp. 3847-3854.
Greenberg, Philip D., Adoptive T Cell Therapy of Tumors: Mechanisms Operative in the Recognition and Elimination of Tumor Cells, Advances in Immunology, vol. 49, 1991, pp. 281-355.
Reusser, Pierre et al., Cytotoxic T-Lymphocyte Response to Cytomegalovirus After Human Allogeneic Bone Marrow Transplantation: Pattern of Recovery and Correlation With Cytomegalovirus Infection and Disease, Blood, vol. 78, No. 5, 1991, pp. 1373-1380.
Riddell, Stanley R. et al., Class I MHC-Restricted Cytotoxic T Lymphocyte Recognition of Cells Infected with Human Cytomegalvirus does not Require Endogenous Viral Gene Expression, The Journal of Immunology, vol. 146, No. 8, 1991, pp. 2795-2804.
Riddell, Stanley R. et al., The use of anti-CD3 and anti CD28 monoclonal antibodies to clone and expand human antigen-specific T cells, Journal of Immunological Methods, vol. 128, 1990, pp. 189-201.
Rosenberg, Steven A. et al., A Progress Report on the Treatment of 157 Patients with Advanced Cancer using Lymphokine-Activated Killer Cells and Interleukin-2 or High dose Interleukin-2 Alone, The New England Journal of Medicine, vol. 316, No. 15, 1987, pp. 889-897.
Rosenberg, Steven A. et al., Use of Tumor-Infiltrating Lymphocytes and Interleukin-2 in the Immunotherapy of Patients with Metastatic Melanoma, The New England Journal of Medicine; vol. 319, No. 25,1988, pp. 1676-1680.
Ho, Monto et al., A Phase 1 Study of Adoptive Transfer of Autologous CD8[+] T Lymphocytes in Patients With Acquired Immunodeficiency Syndrome (AIDS) Related Complex or AIDS, Blood, vol. 81, No. 8, 1993, pp. 2093-2101.
Koberda, Jaroslaw et al., Effect of anti-CD3/anti-CD28/interleukin-2 stimulation of mononuclear cells on transforming growth factor β inhibition of lymphokine-activated killer cell generation, J Cancer Res. Clinical Oncology, No. 119, vol. 3, 1993, pp. 131-136.
Petersen, Torben E. et al., (Edited by Deane F. Mosher), Primary Structure of Fibronectin, Fibronectin,1989, pp. 1-24.

Kimizuka, Fusao et al., Production and Characterization of Functional Domains of Human Fibronectin Expressed in *Escherichia coli*, Journal of Biochemistry, vol. 110, No. 2, 1991, pp. 284-291.
Hanenberg, Helmut et al., Optimization of Fibronectin-Assisted Retroviral Gene Transfer into Human CD34[+] Hematopoietic Cells, Human Gene Therapy, vol. 8, 1997, pp. 2193-2206.
Ruoslahti, Erkki et al., Alignment of Biologically Active Domains in the Fibronectin Molecule, The Journal of Biological Chemistry, vol. 256, No. 14, Jul. 25, 1981, pp. 7277-7281.
Kornblihtt, Albert R. et al., Primary structure of human fibronectin: differential splicing may generate at least 10 polypeptides from a single gene, The EMBO Journal, vol. 4, No. 7, 1985, pp. 1755-1759.
Sekiguchi, Kiyotoshi et al., Human Liver Fibronectin Complementary DNAs: Identification of Two Different Messenger RNAs Possible Encoding the α and β Subunits of Plasma Fibronectin, Biochemistry, vol. 25, No. 17, 1986, pp. 4938-4941.
Williams, David A. et al., Fibronectin and VLA-4 in Haematopoietic stem cell microenvironment interactions, of Nature, vol. 352, 1991, pp. 438-441.
Mikamo, Shinsuke, Bulk Culture of Human Lymphocytes, Cell Technology, vol. 14, No. 2, 1995, pp. 223-227.
Sekine, Teruaki, Bulk Culture method for human lymphocytes for use in adoptive immunotherapy, Cell Culture, vol. 17, No. 6, 1991, pp. 192-195.
Hibino S et al., Tenascin suppresses CD3-mediated T cell activation, Biochem. Biophys. Res. Commun., 1998, vol. 250, p. 119-124.
Halvorson M J et al., α4 and α5 integrins costimulate the CD3-dependent proliferation of fetal thymocytes., Cell. Immunol., 1998, vol. 189, p. 1-9.
Japanese Office Action, dated Nov. 14, 2011, for Japanese Application No. 2007-530976.
United States Office Action for copending U.S. Appl. No. 11/992,661 dated Jul. 12, 2013.
Li et al., "Enhancement of Lymphokine-Activated Killer Cell Activity by Fibronectin," Journal of Immunotherapy, vol. 20, No. 2, pp. 123-130, 1997.
US Office Action for U.S. Appl. No. 10/568,745 dated Dec. 19, 2013.
Ochoa et al., "Long-Term Growth of Lymphokine-Activated Killer (LAK) Cells: Role of Anti-CD3, β-IL 1, Interferon-γ and -β1," The Journal of Immunology, vol. 138, No. 8, Apr. 15, 1987, pp. 2728-2733.
US Office Action for U.S. Appl. No. 10/509,056 dated May 23, 2013.
Canadian Office Action for Application No. 2,479,288 dated Feb. 28, 2012.
Aruga et al., "Enhancement of In Vitro Cytolytic Reactivity of T Cells Stimulated with Tumor-Pulsed Dendritic Cells," Biotherapy, vol. 12, No. 5, May 1998, pp. 875-877 (with English abstract).
Avdalovic et al., "Adhesion and Costimulation of Proliferative Responses of Human T Cells by Interaction of VLA-4 and VLA-5 with Fibronectin", Immunology Letters, vol. 35, 1993, pp. 101-108, XP-002381602.
Azuma et al., "Functional Expression of B7/BB1 on Activated T Lymphocytes", J. Exp. Med., vol. 177, Mar. 1993, pp. 845-850.
Bednarek et al., "The Minimum Peptide Epitope From the Influenza Virus Matrix Protein", The Journal of Immunology, vol. 147, No. 12, Dec. 15, 1991, pp. 4047-4053.
Benigni et al., "Phenotype and Homing of CD4 Tumor-Specific T Cells is Modulated by Tumor Bulk," The Journal of Immunology, 2005, vol. 175, pp. 739-748.
Blue et al., "Enhancement of CD2-Mediated T Cell Activation by the Interaction of VLA-4 with Fibronectin", Cellular Immunology, vol. 138, 1991, pp. 238-244.
BPAI Decision on Appeal dated May 28, 2010, for U.S. Appl. No. 10/344,534.
Cardarelli et al., "Fibronectin Augments Anti-CD3-Mediated IL-2 Receptor (CD25) Expression on Human Peripheral Blood Lymphocytes", Cell Immunol., vol. 135, pp. 105-117, 1991.
Carter et al., "Development and maintenance of bovine cytotoxic lymphocytes with recombinant human interleukin-2," Immunology, vol. 57, 1986, pp. 123-129.
Chen et al., "Retroviral Transduction of Protein Kinase C- into Tumor-Specific T Cells Allows Antigen-Independent long-Term

(56) References Cited

OTHER PUBLICATIONS

Growth in IL-2 with Retention of Functional Specificity in Vitro and Ability to Mediate Tumor Therapy in Vivo", J. Immunol., vol. 153, 1994, pp. 3630-3638.

Chinese Office Action with English translation dated Jan. 15, 2010, for Application No. 200480024172.7.

Chinese Office Action with English translation dated Nov. 30, 2007, for Application No. 200480024172.7.

Dardalhon et al., "Highly efficient gene transfer in naive human T cells with a murine leukemia virus-based vector," Blood, vol. 96, No. 3, Aug. 1, 2000, pp. 885-893.

Davis et al., "Fibronectin Promotes Proliferation of Naive and Memory T Cells by Signaling Through Both The VLA-4 and VLA-5 Intergin Molecules", The Journal of Immunology, vol. 145, No. 3, Aug. 1, 1990, pp. 785-793.

del Pozo et al., "Chemokines Regulate Cellular Polarization and Adhesion Receptor Redistribution During Lymphocyte Interaction with Endothelium and Extracellular Matrix, Involvement of cAMP Signaling Pathway", The Journal of Cell Biology, vol. 131, No. 2, Oct. 1, 1995, pp. 495-506.

Extended European Search Report for Application No. EP 09004189. 8, dated Dec. 8, 2009.

Freshney, "Animal Cell Culture", Ed. 1986, IRL Press, Oxford, Washington, DC, Sections 2.1, 3.2.2-3.2.6, 5, 6.1-6.3, 3.1-3.4.

Freshney, "Animal Cell Culture: A Practical Approach", IRL Press, Oxford, Washington, DC, 1986, pp. 26-41.

Funaro et al., "Stimulation of T Cells via CD44 Requires Leukoyte-Function-Associated Antigen Interactions and Interleukin-2 Production, Human Immunology", vol. 40, No. 4, Aug. 1994, pp. 267-278.

Galandrini et al., "Hyaluronate is Costimulatory for Human T Cell Effector Functions and Binds to CD44 on Activated T Cells", J. Immunol., vol. 153, 1994, pp. 21-31.

Galandrini et al., "Antibodies to CD44 Trigger Effector Functions of Human T Cell Clones", J. Immunol., vol. 150, No. 10, May 15, 1993, pp. 4225-4235.

Galandrini et al., "CD44 Triggering Enhanced Human NK Cell Cytotoxic Functions", J. Immunol., vol. 153, No. 10, pp. 4399-4407, Nov. 15, 1994 (Abstract only).

Galandrini et al., "Ligation of the Lymphocyte Homing Receptor CD44 Triggers T-Helper and Cytolytic Functions of Human T-Cells", Cytotechnology, 1993, vol. 11, Suppl. 1, pp. S100-S102 (abstract only).

Gallagher et al., Interleukin-3 and Interleukin-4 each strongly inhibit the induction and function of human LAK cells°, Clin. exp. Immunol., 1988, vol. 74, pp. 166-170.

Gattinoni et al., "Acquisition of full effector function in vitro paradoxically impairs the in vivo antitumor efficacy of adoptively transferred CD8+ T cells," J. Clin. Invest., vol. 115, No. 6, Jun. 2005, pp. 1616-1626.

Genetic Medicine, vol. 3, No. 2, 1999, pp. 114-119, with partial English translation.

GIBCO/Invitrogen Publication, "A Guide to Serum-Free Cell Culture", 2003, 7 pages.

Greenberg, "Adoptive T Cell Therapy of Tumors: Mechanisms Operative in the Recognition and Elimination of Tumor Cells", Advances in Immunology, vol. 49, 1991, pp. 281-355.

Hanenberg et al., "Optimization of Fibronectin-Assisted Retroviral Gene Transfer into Human CD34+ Hematopoietic Cells", Human Gene Therapy, vol. 8, Dec. 10, 1997, pp. 2193-2206.

Ideno et al., "Novel expansion methods of CTL using recombinant fibronectin fragments," Dai 62 Kai Annual Meeting of the Japan Cancer Association Kiji, Sep. 25-27, 2003, pp. 175.

Ideno et al., "T Cell expansion using RetroNectin(II): RN-T cells contain high portion of Naive T-like cells and show high ability of antigen recognition," Dai 65 Kai Annual Meeting of the Japan Cancer Association Kiji, Aug. 28, 2006, pp. 330.

International Preliminary Report on Patentability with an English translation dated Apr. 1, 2008, for International Application No. PCT/JP2006/319105.

International Preliminary Report on Patentability with an English translation dated Feb. 20, 2008, for International Application No. PCT/JP2006/315881.

International Search Report dated Dec. 3, 2002 for International Application No. PCT/JP02/08298.

International Search Report dated Nov. 27, 2001, for Application No. PCT/JP01/07032.

International Search Report with the English translation dated Jan. 9, 2007, for Application No. PCT/JP2006/319105.

International Search Report with the English translation dated Oct. 10, 2006, for Application No. PCT/JP2006/315861.

Janeway and Travers, Immunobiology: The Immune System in Health and Disease, 1997, p. 4:2.

Japanese Office Action dated Mar. 5, 2010, for Application No. 2005-513357.

Johnson et al. "Expression and Function of Insulin-Like Growth Factor Receptors on Anti-CD3-Activated Human T Lymphocytes", Journal of Immunology, vol. 148, No. 1, Jan. 1, 1992, pp. 63-71.

Johnston et al., "Induction of B16 Melanoma Melanogenesis by a Serum-Free Synthetic Medium," Experimental Cell Research, vol. 201, 1992, pp. 91-96.

Jung et al., "Induction of Cytotoxicity in Human Peripheral Blood Mononuclear Cells by Monoclonal Antibody OKTS", Journal of Immunology, vol. 139, No. 2, Jul. 15, 1987, pp. 639-644.

Kaldjian et al., "Enhancement of lymphocyte proliferation assays by use of serum-free medium", Journal of Immunological Methods, vol. 147, No. 2, 1992, pp. 189-195.

Kanto et al., "Neutralization of Transforming Growth Factor-1 Augments Hepatitis C Virus-Specific Cytotoxic T Lymphocyte Induction In Vitro", Journal of Clinical Immunology, vol. 17, No. 6, 1997, pp. 462-471.

Kato et al., Jpn. J. Phycol. (Sorui), vol. 48, Mar. 10, 2000, pp. 13-19.

Katzman et al., "Fibronectin and Cellular Cytotoxicity. Evidence Against a Role for Fibronectin in Natural Killer Activity", J. Lab. Clin. Med., vol. 110, No. 1, Jul. 1987, pp. 75-82.

Kornblihtt et al., "Isolation and Characterization of cDNA Clones for Human and Bovine Fibronectins", Proc. Natl. Acad. Sci. USA, vol. 80, No. 16, Jun. 1983, pp. 3218-3222.

Kornblihtt et al., "The Fibronectin Gene as a Model for Splicing and Transcription Studies", FASEB Journal, vol. 10, 1996, pp. 248-257.

Lehnert et al., "MAdCAM-1 costimulates T cell proliferation exclusively through integrin •4•7, whereas VCAM-1 and CS-1 peptide use •4•1: evidence for "remote" costimulation and induction of hyperresponsiveness to B7 molecules", Eur. J. Immunol., vol. 28, 1998, pp. 3605-3615.

Lucivero et al., "Functional Characteristics of Cord Blood T Lymphocytes After Lectin and Anti-CD3 Stimulation", Int. J. Clin. Lab. Res., vol. 26, 1996, pp. 255-261.

Matsuyama et al., "Activation of CD4 cells by fibronectin and anti-CD3 antibody. A synergistic effect mediated by the VLA-5 fibronectin receptor complex." J. Exp. Med., vol. 170, No. 4, Oct. 1989, pp. 1133-1148.

Mazumder et al., "Phase I Study of the Adoptive Immunotherapy of Human Cancer with Lectin Activated Autologous Mononuclear Cells", Cancer, vol. 53, No. 4, Feb. 1984, pp. 896-905.

Mizobata et al., "Fibronectin promotes the proliferation of cytotoxic T lymphocytes generated from cancer patients", British Journal of Cancer, vol. 74, 1996, pp. 1598-1604, XP008058177.

Mizobata, "Study of Fibronectin on the Proliferation and the Activation of Cytotoxic T Lymphocytes Generated by Immobolized Anti-CD3 Monoclonal Antibody and Interleukin-2". J. Wakayama Med. Soc., vol. 46, No. 4, pp. 457-467, 1995.

Muraki et al., "T cell expansion using RetroNectin (I), Useful method to expand T cells, characterized by high portion of Naive T-like cells," Dai 65 Kai Annual Meeting of the Japan Cancer Association Kiji, Aug. 28, 2006, pp. 330.

Neri et al., Calcein-Acetyoxymethyl Cytotoxicity Assay: Standardization of a Method Allowing Additional Analyses on Recovered Effector Cells and Supematants°, Clin. and Diag. Lab. Immunol., vol. 8, No. 6, Nov. 2001, pp. 1131-1135.

Noguchi et al., "Polysaccharide Preparation PSK Augments the Proliferation and Cytotoxicity of Tumor-Infiltrating Lymphocytes in Vitro," Anticancer Research, vol. 15, 1995, pp. 255-258.

(56) References Cited

OTHER PUBLICATIONS

NUNCION Product Information, VWR workshop, p. 1, website search date Apr. 19, 2007, http://vwrlabshop.com/product.asp_Q_pn_E_0013575.
Ochoa et al., "Lymphokine-Activated Killer Activity in Long-Term Cultures with Anti-CD3 Plus Interleukin 2: Identification and Isolation of Effector Subsets", Cancer Research, vol. 49, Feb. 15, 1989, pp. 963-968.
Ostergaard et al., "Fibronectin Induces Phosphorylation of a 120-kDa Protein and Synergizes with the T Cell Receptor to Activate Cytotoxic T Cell Clones", Eur. J. Immunol., vol. 25, 1995, pp. 252-256.
Palmieri et al., "Cross-Linking of a Journal of •4•1 and a5β1 Fibronectin Receptors Enhances Natural Killer Cell Cytotoxic Activity", Journal of Immunology, vol. 155, 1995, pp. 5314-5322, XP002381601.
Parhar et al., "Anti-tumor cytotoxic potential and effect on human bone marrow GM-CFU of human LAK cells generated in response to various cytokines", Eur. Cytokine Netw., vol. 3, No. 3, May-Jun. 1992, pp. 299-306.
Parker et al., "Expansion and Characterization of T Cells Transduced with a Chimeric Receptor against Ovarian Cancer," Human Gene Therapy, vol. 11, Nov. 20, 2000, pp. 2377-2387.
Partial European Search Report in European Application No. 09004189.8 mailed Aug. 3, 2009.
Paul et al., "Long-term growth and cloning of non-transformed lymphocytes", Nature. vol. 294, Dec. 24/31, 1981, pp. 697-699.
Pawelec et al., "Extrathymic T Cell Differentiation in Vitro From Human CD34+ Stem Cells", Journal of Leukocyte Biology, vol. 64, Dec. 1998, pp. 733-739.
Pierschbacher et al., "Location of the Cell-Attachment Site in Fibronectin with Monoclonal Antibodies and Proteolytic Fragments of the Molecule", Cell, vol. 26, No. 2, Oct. 1981, pp. 259-267, XP-002381662.
Pollock et al., "High-Efficiency Gene Transfer into Normal and Adenosine Deaminase-Deficient T Lymphocytes is Mediated by Transduction on Recombinant Fibronectin Fragments", Journal of Virology, vol. 72, No. 6, Jun. 1998, pp. 4882-4892.
Retronectin, 2010, Takara Bio, Inc., http://catalog.takara-bio.co.jp/en/PDFFiles/T100A_B_e.pdf. pp. 1-8.
Reusser et al., "Cytotoxic T-Lymphocyte Response to Cytomegalovirus After Human Allogenic Bone Marrow Transplantation. Pattern of Recovery and Correlation with Cytomegalovirus Infection and Disease", Blood, vol. 78, No. 5, Sep. 1, 1991, pp. 1373-1380.
Riddell et al., "Restoration of Viral Immunity in Immunodeficient Humans by the Adoptive Transfer of T Cell Clones", Science. vol. 257, No. 5067, Jul. 10, 1992, pp. 238-241.
Rider et al., "Phorbol Diesters and Dioctanoylglycerol Stimulate Accumulation of Both Diacylglycerols and Alkylacylglycerols in Human Neutrophils", The Journal of Immunology, vol. 140, No. 1, Jan. 1, 1988, pp. 200-207.
Rosenberg et al., "Use of Tumor-Infiltrating Lymphocytes and Interleukin-2 in the Immunotherapy of Patients with Metastatic Melanoma", The New England Journal of Medicine, vol. 319, No. 25, Dec. 22, 1988, pp. 1676-1680.
Rostagno et al., "Comparison of the Fibrin-Binding Activities in the N- and C-termini of Fibronectin", Biochem. J. vol. 338, 1999, pp. 375-385.
Sagawa et al., "Improvement of LAK cells expansion method with combined use of RetroNectin and anti-CD3 antibody," Dai 62 Kai Annual Meeting of the Japan Cancer Association Kiji, 2003, p. 438.
Seth et al., "T-Cell-Receptor-Independent Activation of Cytolytic Activity of Cytotoxic T Lymphocytes Mediated Through CD44 and gp90MEL-14", Proc. Natl. Acad. Sci. U.S.A., vol. 88, No. 17, Sep. 1991, pp. 7877-7881.
Shimizu et al., "Costimulation of Proliferative Repsonses of Resting CD4+ T Cells by the Interaction of VLA-4 and VLA-5 With Fibronectin of VLA-6 with Laminin", The Journal of Immunology, vol. 145, No. 1, Jul. 1, 1990, pp. 59-67, XP002362286.
Shun et al., "An experimental study on immunoregulatory effect of fucoidan", vol. 14, No. 3, 1995, pp. 9-13, with English abstract.
Shuqin et al., "Induction of Allogenic Cytotoxic T Lymphocytes and Their Culture", Journal of South China Normal University (Natural Science Edition), No. 4, 1994, pp. 11-17 (including partial English language translation).
Sigma-Aldrich Product sheet for "1,2-Dioctanoyl-sn-glycerol", 2 pages, downloaded on Mar. 8, 2011 from sigmaaldrich.com/catalog/ProductDetail.do?D7=0&N5=SEARCH_CONCAT_PNO%7CBRAND_KEY&N4=D5156%7CSIGMA&N25=O&QS=ON&F=SPEC.
Simon et al., The outer surface lipoprotein A of *Borrelia burgdorferi* provides direct and indirect augmenting/co-stimulatory signals for the activation of CD4+ and CD8+ T cells, Immunol. Lett., 1995, vol. 46, No. 3, pp. 137-142.
Stohl et al., "Generation of Cytolytic Activity with Anti-CD3 Monoclonal Antibodies Involves Both IL-2-Independent and -Dependent Components", J. Immunol., vol. 144, No. 10, May 15, 1990, pp. 3718-3725.
Takahashi et al., "Antigen-Independent T Cell Activation Mediated by a Very Late Activation Antigen-Like Extracellular Matrix Receptor", Eur. J. Immunol., vol. 21, 1991, pp. 1559-1562.
Tamura et al., "Expression and Function of c-Met, a Receptor for Hepatocyte Growth Factor, During T-Cell Development", Scandinavian Journal of Immunology, 1998, vol. 47, pp. 298-301.
Tani et al., "Cancer Therapy & Host", vol. 12, No. 4, 2000, pp. 330-336.
U.S. Advisory Action dated Apr. 2, 2010, for U.S. Appl. No. 11/790,025.
U.S. Advisory Action dated, Jan. 18, 2008, for U.S. Appl. No. 10/344,534.
U.S. Advisory Action dated, May 6, 2008, for U.S. Appl. No. 10/509,055.
U.S. Advisory Action dated, Sep. 24, 2007, for U.S. Appl. No. 10/344,534.
U.S. Communication dated, Jul. 23, 2009, for U.S. Appl. No. 10/344,534.
U.S. Examiner's Interview Summary dated, Jun. 4, 2008, for U.S. Appl. No. 10/344,534.
U.S. Interview Summary dated Jun. 7, 2010, for U.S. Appl. No. 11/831,423.
U.S. Interview Summary dated, Aug. 2, 2007, for U.S. Appl. No. 10/486,512.
U.S. Interview Summary dated, Feb. 5, 2008, for U.S. Appl. No. 10/344,534.
U.S. Interview Summary dated, Mar. 19, 2007, for U.S. Appl. No. 10/344,534.
U.S. Notice of Allowance dated, Jun. 15, 2010, for U.S. Appl. No. 10/344,534.
U.S. Office Action dated Feb. 23, 2009, for U.S. Appl. No. 10/509,055.
U.S. Office Action dated Jun. 18, 2009, for U.S. Appl. No. 10/344,534.
U.S. Office Action dated Jun. 9, 2011, for U.S. Appl. No. 11/992,651.
U.S. Office Action dated Mar. 17, 2005, for U.S. Appl. No. 10/509,055.
U.S. Office Action dated Oct. 14, 2010, for U.S. Appl. No. 11/992,661.
U.S. Office Action dated, Apr. 14, 2010, for U.S. Appl. No. 10/509,056.
U.S. Office Action dated, Apr. 19, 2010, for U.S. Appl. No. 10/488,512.
U.S. Office Action dated, Apr. 24, 2006, for U.S. Appl. No. 10/486,512.
U.S. Office Action dated, Aug. 21, 2008, for U.S. Appl. No. 10/509,055.
U.S. Office Action dated, Dec. 18, 2009, for U.S. Appl. No. 11/790,025.
U.S. Office Action dated, Dec. 21, 2007, for U.S. Appl. No. 10/509,055.
U.S. Office Action dated, Dec. 28, 2010, for U.S. Appl. No. 11/992,661.

(56) References Cited

OTHER PUBLICATIONS

U.S. Office Action dated, Feb. 10, 2011, for U.S. Appl. No. 10/509,055.
U.S. Office Action dated, Feb. 23, 2007, for U.S. Appl. No. 10/486,512.
U.S. Office Action dated, Jan. 18, 2008, for U.S. Appl. No. 10/344,534.
U.S. Office Action dated, Jan. 29, 2007, for U.S. Appl. No. 10/509,056.
U.S. Office Action dated, Jan. 5, 2009, for U.S. Appl. No. 10/466,512.
U.S. Office Action dated, Jan. 5, 2009, for U.S. Appl. No. 11/790,025.
U.S. Office Action dated, Jul. 12, 2010, for U.S. Appl. No. 10/566,745.
U.S. Office Action dated, Jul. 25, 2008, for U.S. Appl. No. 10/486,512.
U.S. Office Action dated, Jul. 26, 2010, for U.S. Appl. No. 10/344,534.
U.S. Office Action dated, Jul. 6, 2011, for U.S. Appl. No. 10/509,055.
U.S. Office Action dated, Jul. 9, 2009, for U.S. Appl. No. 10/568,745.
U.S. Office Action dated, Jun. 20, 2005, for U.S. Appl. No. 10/344,534.
U.S. Office Action dated, Jun. 23, 2009, for U.S. Appl. No. 10/486,512.
U.S. Office Action dated, Jun. 25, 2004, for U.S. Appl. No. 10/486,512.
U.S. Office Action dated, Jun. 9, 2009, for U.S. Appl. No. 10/509,055.
U.S. Office Action dated, Mar. 18, 2010, for U.S. Appl. No. 11/831,423.
U.S. Office Action dated, Mar. 18, 2011, for U.S. Appl. No. 10/568,745.
U.S. Office Action dated, Mar. 28, 2006, for U.S. Appl. No. 10/344,534.
U.S. Office Action dated, Mar. 5, 2009, for U.S. Appl. No. 11/831,423.
U.S. Office Action dated, May 11, 2007, for U.S. Appl. No. 10/509,055.
U.S. Office Action dated, May 13, 2008, for U.S. Appl. No. 10/344,534.
U.S. Office Action dated, May 16, 2007, for U.S. Appl. No. 10/344,534.
U.S. Office Action dated, May 27, 2009, for U.S. Appl. No. 11/831,423.
U.S. Office Action dated, May 30, 2008, for U.S. Appl. No. 10/486,512.
U.S. Office Action dated, May 7, 2009, for U.S. Appl. No. 11/790,025.
U.S. Office Action dated, Nov. 22, 2010, for U.S. Appl. No. 10/486,512.
U.S. Office Action dated, Nov. 24, 2009, for U.S. Appl. No. 10/344,534.
U.S. Office Action dated, Nov. 27, 2009, for U.S. Appl. No. 10/568,745.
U.S. Office Action dated, Nov. 4, 2009, for U.S. Appl. No. 11/831,423.
U.S. Office Action dated, Nov. 6, 2009, for U.S. Appl. No. 10/344,534.
U.S. Office Action dated, Oct. 10, 2007, for U.S. Appl. No. 10/486,512.
U.S. Office Action dated, Oct. 11, 2005, for U.S. Appl. No. 10/344,534.
U.S. Office Action dated, Oct. 22, 2010, for U.S. Appl. No. 10/509,055.
U.S. Office Action dated, Oct. 25, 2010, for U.S. Appl. No. 10/568,745.
U.S. Office Action dated, Oct. 29, 2010, for U.S. Appl. No. 10/486,512.
U.S. Office Action dated, Oct. 30, 2008, for U.S. Appl. No. 10/568,745.
U.S. Office Action dated, Sep. 25, 2006, for U.S. Appl. No. 10/344,534.
U.S. Office Action dated, Sep. 3, 2009, for U.S. Appl. No. 10/509,055.
U.S. Office Action dated, Sep. 30, 2009, for U.S. Appl. No. 10/486,512.
Uberti et al., "Preclinical Studies Using Immobilized OKT3 to Activate Human T Cells for Adoptive Immunotherapy. Optimal Conditions for the Proliferation and Induction of Non-MHC-Restricted Cytotoxicity", Clinical Immunology and Immunopathology, vol. 70, No. 3, Mar. 1994, pp. 234-240.
van der Loo et al., VLA-5 is Expressed by Mouse and Human Long-Term Repopulating Hematopoietic Cells and Mediates Adhesion to Extracellular Matrix Protein Fibronectin, J. Clin. Invest., vol. 102, No. 5, Sep. 1998, pp. 1051-1061.
Wills, M. R., et al., "Identification of Naive or Antigen-Experienced Human CD8+ T Cells by Expression of Costimulation and Chemokine Receptors. Analysis of the Human Cytomegalovirus-Specific CD8+ T Cell Response," The Journal of Immunology, 2002, vol. 168, pp. 5455-5464.
Wolf et al., "Leukapheresis for the extraction of monocytes and various lymphocyte subpopulations from peripheral blood: product quality and prediction of the yield using different harvest procedures", Vox Sanguinis, vol. 88, 2005, pp. 249-255.
Ybarrondo et al., "Cytotoxic T-lymphocyte interaction with fibronectin and vitronectin: activated adhesion and cosignaling", Immunology, vol. 91, 1997, pp. 186-192.
Yoneda et al., "Role of the Heparin-Binding Domain of Chimeric Peptides Derived from Fibronectin in Cell Spreading and Motility", Experimental Cell Research, vol. 217, pp. 169-179, 1995.
Yu et al., "The Study of Human LAK and LI-LAK Cells' Proliferation and Activation of Antitumor in Vitro", Journal of Jinan University, Natural Science & Medicine Edition, vol. 19 Suppl., Dec. 1998, pp. 56-60.
English translation of the Japanese Office Action dated Nov. 14, 2011, for Application No. 2007-530976.

* cited by examiner

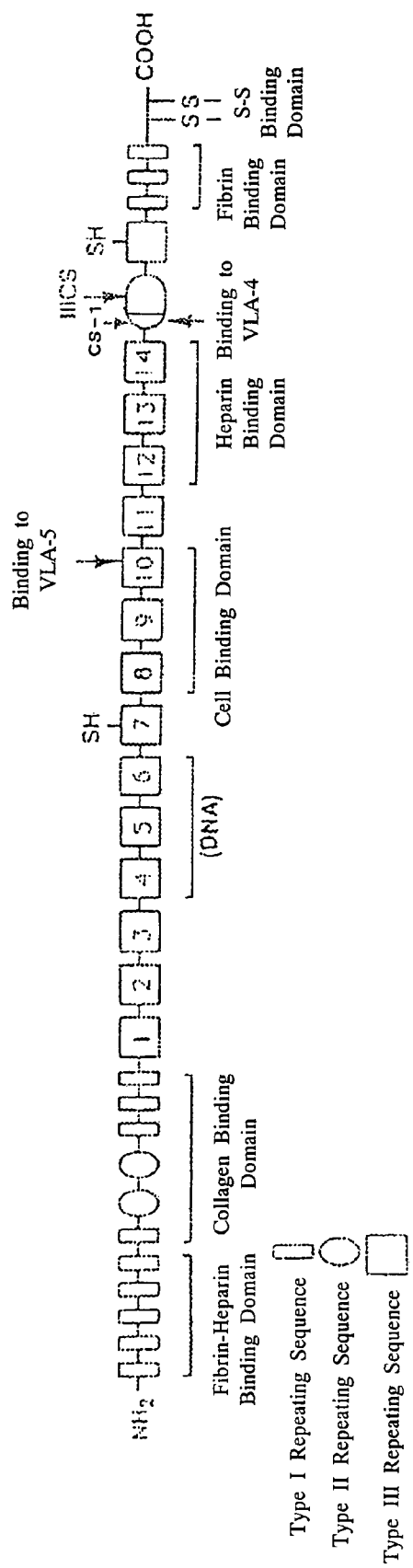

```
                        SEQUENCE LISTING

<160> NUMBER OF SEQ ID NOS: 21

<210> SEQ ID NO 1
<211> LENGTH: 87
<212> TYPE: PRT
<213> ORGANISM: Artificial Sequence
<220> FEATURE:
<223> OTHER INFORMATION: partial region of fibronectin named III-8

<400> SEQUENCE: 1

Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
        35                  40                  45

Pro Ser Asp Asn Ala Val Val Leu Thr Asn Leu Leu Pro Gly Thr Glu
    50                  55                  60

Tyr Val Val Ser Val Ser Ser Val Tyr Glu Gln His Glu Ser Thr Pro
65                  70                  75                  80

Leu Arg Gly Arg Gln Lys Thr
                85

<210> SEQ ID NO 2
<211> LENGTH: 90
<212> TYPE: PRT
<213> ORGANISM: Artificial Sequence
<220> FEATURE:
<223> OTHER INFORMATION: partial region of fibronectin named III-9

<400> SEQUENCE: 2

Gly Leu Asp Ser Pro Thr Gly Ile Asp Phe Ser Asp Ile Thr Ala Asn
1               5                   10                  15

Ser Phe Thr Val His Trp Ile Ala Pro Arg Ala Thr Ile Thr Gly Tyr
            20                  25                  30

Arg Ile Arg His His Pro Glu His Phe Ser Gly Arg Pro Arg Glu Asp
        35                  40                  45

Arg Val Pro His Ser Arg Asn Ser Ile Thr Leu Thr Asn Leu Thr Pro
    50                  55                  60

Gly Thr Glu Tyr Val Val Ser Ile Val Ala Leu Asn Gly Arg Glu Glu
65                  70                  75                  80

Ser Pro Leu Leu Ile Gly Gln Gln Ser Thr
                85                  90

<210> SEQ ID NO 3
<211> LENGTH: 94
<212> TYPE: PRT
<213> ORGANISM: Artificial Sequence
<220> FEATURE:
<223> OTHER INFORMATION: partial region of fibronectin named III-10

<400> SEQUENCE: 3

Val Ser Asp Val Pro Arg Asp Leu Glu Val Val Ala Ala Thr Pro Thr
```

```
                        1               5                  10                 15
Ser Leu Leu Ile Ser Trp Asp Ala Pro Ala Val Thr Val Arg Tyr Tyr
                       20                 25                30
Arg Ile Thr Tyr Gly Glu Thr Gly Gly Asn Ser Pro Val Gln Glu Phe
             35                 40                 45
Thr Val Pro Gly Ser Lys Ser Thr Ala Thr Ile Ser Gly Leu Lys Pro
     50                 55                 60
Gly Val Asp Tyr Thr Ile Thr Val Tyr Ala Val Thr Gly Arg Gly Asp
65                 70                 75                 80
Ser Pro Ala Ser Ser Lys Pro Ile Ser Ile Asn Tyr Arg Thr
                 85                 90

<210> SEQ ID NO 4
<211> LENGTH: 84
<212> TYPE: PRT
<213> ORGANISM: Artificial Sequence
<220> FEATURE:
<223> OTHER INFORMATION: partial region of fibronectin named III-11

<400> SEQUENCE: 4

Gln Met Gln Val Thr Asp Val Gln Asp Asn Ser Ile Ser Val Lys Trp
1               5                  10                 15
Leu Pro Ser Ser Ser Pro Val Thr Gly Tyr Arg Val Thr Thr Thr Pro
                20                 25                 30
Lys Asn Gly Pro Gly Pro Thr Lys Thr Lys Thr Ala Gly Pro Asp Gln
             35                 40                 45
Thr Glu Met Thr Ile Glu Gly Leu Gln Pro Thr Val Glu Tyr Val Val
     50                 55                 60
Ser Val Tyr Ala Gln Asn Pro Ser Gly Glu Ser Gln Pro Leu Val Gln
65                 70                 75                 80
Thr Ala Val Thr

<210> SEQ ID NO 5
<211> LENGTH: 92
<212> TYPE: PRT
<213> ORGANISM: Artificial Sequence
<220> FEATURE:
<223> OTHER INFORMATION: partial region of fibronectin named III-12

<400> SEQUENCE: 5

Ala Ile Pro Ala Pro Thr Asp Leu Lys Phe Thr Gln Val Thr Pro Thr
1               5                  10                 15
Ser Leu Ser Ala Gln Trp Thr Pro Pro Asn Val Gln Leu Thr Gly Tyr
                20                 25                 30
Arg Val Arg Val Thr Pro Lys Glu Lys Thr Gly Pro Met Lys Glu Ile
             35                 40                 45
Asn Leu Ala Pro Asp Ser Ser Ser Val Val Val Ser Gly Leu Met Val
     50                 55                 60
Ala Thr Lys Tyr Glu Val Ser Val Tyr Ala Leu Lys Asp Thr Leu Thr
65                 70                 75                 80
Ser Arg Pro Ala Gln Gly Val Val Thr Thr Leu Glu
                 85                 90

<210> SEQ ID NO 6
<211> LENGTH: 89
<212> TYPE: PRT
<213> ORGANISM: Artificial Sequence
<220> FEATURE:
<223> OTHER INFORMATION: partial region of fibronectin named III-13
```

<400> SEQUENCE: 6

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
            20                  25                  30

Gln Val Asp Ala Val Pro Ala Asn Gly Gln Thr Pro Ile Gln Arg Thr
        35                  40                  45

Ile Lys Pro Asp Val Arg Ser Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 7
<211> LENGTH: 90
<212> TYPE: PRT
<213> ORGANISM: Artificial Sequence
<220> FEATURE:
<223> OTHER INFORMATION: partial region of fibronectin named III-14

<400> SEQUENCE: 7

Ala Ile Asp Ala Pro Ser Asn Leu Arg Phe Leu Ala Thr Thr Pro Asn
1               5                   10                  15

Ser Leu Leu Val Ser Trp Gln Pro Pro Arg Ala Arg Ile Thr Gly Tyr
            20                  25                  30

Ile Ile Lys Tyr Glu Lys Pro Gly Ser Pro Pro Arg Glu Val Val Pro
        35                  40                  45

Arg Pro Arg Pro Gly Val Thr Glu Ala Thr Ile Thr Gly Leu Glu Pro
    50                  55                  60

Gly Thr Glu Tyr Thr Ile Tyr Val Ile Ala Leu Lys Asn Asn Gln Lys
65                  70                  75                  80

Ser Glu Pro Leu Ile Gly Arg Lys Lys Thr
                85                  90

<210> SEQ ID NO 8
<211> LENGTH: 25
<212> TYPE: PRT
<213> ORGANISM: Artificial Sequence
<220> FEATURE:
<223> OTHER INFORMATION: partial region of fibronectin named CS-1

<400> SEQUENCE: 8

Asp Glu Leu Pro Gln Leu Val Thr Leu Pro His Pro Asn Leu His Gly
1               5                   10                  15

Pro Glu Ile Leu Asp Val Pro Ser Thr
            20                  25

<210> SEQ ID NO 9
<211> LENGTH: 274
<212> TYPE: PRT
<213> ORGANISM: Artificial Sequence
<220> FEATURE:
<223> OTHER INFORMATION: fibronectin fragment named C-274

<400> SEQUENCE: 9

Pro Thr Asp Leu Arg Phe Thr Asn Ile Gly Pro Asp Thr Met Arg Val
1               5                   10                  15

Thr Trp Ala Pro Pro Pro Ser Ile Asp Leu Thr Asn Phe Leu Val Arg

```
            20                  25                  30
Tyr Ser Pro Val Lys Asn Glu Glu Asp Val Ala Glu Leu Ser Ile Ser
        35                  40                  45

Pro Ser Asp Asn Ala Val Val Leu Thr Asn Leu Leu Pro Gly Thr Glu
 50                  55                  60

Tyr Val Val Ser Val Ser Ser Val Tyr Glu Gln His Glu Ser Thr Pro
 65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
        115                 120                 125

Ser Gly Arg Pro Arg Glu Asp Arg Val Pro His Ser Arg Asn Ser Ile
    130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
        195                 200                 205

Tyr Arg Ile Thr Tyr Gly Glu Thr Gly Gly Asn Ser Pro Val Gln Glu
    210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
            260                 265                 270

Ile Asp

<210> SEQ ID NO 10
<211> LENGTH: 271
<212> TYPE: PRT
<213> ORGANISM: Artificial Sequence
<220> FEATURE:
<223> OTHER INFORMATION: fibronectin fragment named H-271

<400> SEQUENCE: 10

Ala Ile Pro Ala Pro Thr Asp Leu Lys Phe Thr Gln Val Thr Pro Thr
 1               5                  10                  15

Ser Leu Ser Ala Gln Trp Thr Pro Pro Asn Val Gln Leu Thr Gly Tyr
                20                  25                  30

Arg Val Arg Val Thr Pro Lys Glu Lys Thr Gly Pro Met Lys Glu Ile
            35                  40                  45

Asn Leu Ala Pro Asp Ser Ser Ser Val Val Val Ser Gly Leu Met Val
 50                  55                  60

Ala Thr Lys Tyr Glu Val Ser Val Tyr Ala Leu Lys Asp Thr Leu Thr
 65                  70                  75                  80

Ser Arg Pro Ala Gln Gly Val Val Thr Thr Leu Glu Asn Val Ser Pro
                85                  90                  95

Pro Arg Arg Ala Arg Val Thr Asp Ala Thr Glu Thr Thr Ile Thr Ile
            100                 105                 110
```

```
Ser Trp Arg Thr Lys Thr Glu Thr Ile Thr Gly Phe Gln Val Asp Ala
        115                 120                 125

Val Pro Ala Asn Gly Gln Thr Pro Ile Gln Arg Thr Ile Lys Pro Asp
    130                 135                 140

Val Arg Ser Tyr Thr Ile Thr Gly Leu Gln Pro Gly Thr Asp Tyr Lys
145                 150                 155                 160

Ile Tyr Leu Tyr Thr Leu Asn Asp Asn Ala Arg Ser Ser Pro Val Val
                165                 170                 175

Ile Asp Ala Ser Thr Ala Ile Asp Ala Pro Ser Asn Leu Arg Phe Leu
            180                 185                 190

Ala Thr Thr Pro Asn Ser Leu Leu Val Ser Trp Gln Pro Pro Arg Ala
        195                 200                 205

Arg Ile Thr Gly Tyr Ile Ile Lys Tyr Glu Lys Pro Gly Ser Pro Pro
    210                 215                 220

Arg Glu Val Val Pro Arg Pro Arg Pro Gly Val Thr Glu Ala Thr Ile
225                 230                 235                 240

Thr Gly Leu Glu Pro Gly Thr Glu Tyr Thr Ile Tyr Val Ile Ala Leu
                245                 250                 255

Lys Asn Asn Gln Lys Ser Glu Pro Leu Ile Gly Arg Lys Lys Thr
            260                 265                 270

<210> SEQ ID NO 11
<211> LENGTH: 296
<212> TYPE: PRT
<213> ORGANISM: Artificial Sequence
<220> FEATURE:
<223> OTHER INFORMATION: fibronectin fragment named H-296

<400> SEQUENCE: 11

Ala Ile Pro Ala Pro Thr Asp Leu Lys Phe Thr Gln Val Thr Pro Thr
1               5                   10                  15

Ser Leu Ser Ala Gln Trp Thr Pro Pro Asn Val Gln Leu Thr Gly Tyr
            20                  25                  30

Arg Val Arg Val Thr Pro Lys Glu Lys Thr Gly Pro Met Lys Glu Ile
        35                  40                  45

Asn Leu Ala Pro Asp Ser Ser Ser Val Val Val Ser Gly Leu Met Val
    50                  55                  60

Ala Thr Lys Tyr Glu Val Ser Val Tyr Ala Leu Lys Asp Thr Leu Thr
65                  70                  75                  80

Ser Arg Pro Ala Gln Gly Val Val Thr Thr Leu Glu Asn Val Ser Pro
                85                  90                  95

Pro Arg Arg Ala Arg Val Thr Asp Ala Thr Glu Thr Thr Ile Thr Ile
            100                 105                 110

Ser Trp Arg Thr Lys Thr Glu Thr Ile Thr Gly Phe Gln Val Asp Ala
        115                 120                 125

Val Pro Ala Asn Gly Gln Thr Pro Ile Gln Arg Thr Ile Lys Pro Asp
    130                 135                 140

Val Arg Ser Tyr Thr Ile Thr Gly Leu Gln Pro Gly Thr Asp Tyr Lys
145                 150                 155                 160

Ile Tyr Leu Tyr Thr Leu Asn Asp Asn Ala Arg Ser Ser Pro Val Val
                165                 170                 175

Ile Asp Ala Ser Thr Ala Ile Asp Ala Pro Ser Asn Leu Arg Phe Leu
            180                 185                 190

Ala Thr Thr Pro Asn Ser Leu Leu Val Ser Trp Gln Pro Pro Arg Ala
        195                 200                 205
```

```
Arg Ile Thr Gly Tyr Ile Ile Lys Tyr Glu Lys Pro Gly Ser Pro
    210                 215                 220
Arg Glu Val Val Pro Arg Pro Arg Pro Gly Val Thr Glu Ala Thr Ile
225                 230                 235                 240
Thr Gly Leu Glu Pro Gly Thr Glu Tyr Thr Ile Tyr Val Ile Ala Leu
                245                 250                 255
Lys Asn Asn Gln Lys Ser Glu Pro Leu Ile Gly Arg Lys Lys Thr Asp
                260                 265                 270
Glu Leu Pro Gln Leu Val Thr Leu Pro His Pro Asn Leu His Gly Pro
            275                 280                 285
Glu Ile Leu Asp Val Pro Ser Thr
    290                 295

<210> SEQ ID NO 12
<211> LENGTH: 549
<212> TYPE: PRT
<213> ORGANISM: Artificial Sequence
<220> FEATURE:
<223> OTHER INFORMATION: fibronectin fragment named CH-271

<400> SEQUENCE: 12

Pro Thr Asp Leu Arg Phe Thr Asn Ile Gly Pro Asp Thr Met Arg Val
1               5                   10                  15
Thr Trp Ala Pro Pro Pro Ser Ile Asp Leu Thr Asn Phe Leu Val Arg
            20                  25                  30
Tyr Ser Pro Val Lys Asn Glu Glu Asp Val Ala Glu Leu Ser Ile Ser
        35                  40                  45
Pro Ser Asp Asn Ala Val Val Leu Thr Asn Leu Leu Pro Gly Thr Glu
    50                  55                  60
Tyr Val Val Ser Val Ser Ser Val Tyr Glu Gln His Glu Ser Thr Pro
65                  70                  75                  80
Leu Arg Gly Arg Gln Lys Thr Gly Leu Asp Ser Pro Thr Gly Ile Asp
                85                  90                  95
Phe Ser Asp Ile Thr Ala Asn Ser Phe Thr Val His Trp Ile Ala Pro
            100                 105                 110
Arg Ala Thr Ile Thr Gly Tyr Arg Ile Arg His His Pro Glu His Phe
        115                 120                 125
Ser Gly Arg Pro Arg Glu Asp Arg Val Pro His Ser Arg Asn Ser Ile
    130                 135                 140
Thr Leu Thr Asn Leu Thr Pro Gly Thr Glu Tyr Val Val Ser Ile Val
145                 150                 155                 160
Ala Leu Asn Gly Arg Glu Glu Ser Pro Leu Leu Ile Gly Gln Gln Ser
                165                 170                 175
Thr Val Ser Asp Val Pro Arg Asp Leu Glu Val Val Ala Ala Thr Pro
            180                 185                 190
Thr Ser Leu Leu Ile Ser Trp Asp Ala Pro Ala Val Thr Val Arg Tyr
        195                 200                 205
Tyr Arg Ile Thr Tyr Gly Glu Thr Gly Gly Asn Ser Pro Val Gln Glu
    210                 215                 220
Phe Thr Val Pro Gly Ser Lys Ser Thr Ala Thr Ile Ser Gly Leu Lys
225                 230                 235                 240
Pro Gly Val Asp Tyr Thr Ile Thr Val Tyr Ala Val Thr Gly Arg Gly
                245                 250                 255
Asp Ser Pro Ala Ser Ser Lys Pro Ile Ser Ile Asn Tyr Arg Thr Glu
            260                 265                 270
```

```
Ile Asp Lys Pro Ser Met Ala Ile Pro Ala Pro Thr Asp Leu Lys Phe
            275                 280                 285

Thr Gln Val Thr Pro Thr Ser Leu Ser Ala Gln Trp Thr Pro Pro Asn
    290                 295                 300

Val Gln Leu Thr Gly Tyr Arg Val Arg Val Thr Pro Lys Glu Lys Thr
305                 310                 315                 320

Gly Pro Met Lys Glu Ile Asn Leu Ala Pro Asp Ser Ser Ser Val Val
                325                 330                 335

Val Ser Gly Leu Met Val Ala Thr Lys Tyr Glu Val Ser Val Tyr Ala
            340                 345                 350

Leu Lys Asp Thr Leu Thr Ser Arg Pro Ala Gln Gly Val Val Thr Thr
        355                 360                 365

Leu Glu Asn Val Ser Pro Pro Arg Arg Ala Arg Val Thr Asp Ala Thr
    370                 375                 380

Glu Thr Thr Ile Thr Ile Ser Trp Arg Thr Lys Thr Glu Thr Ile Thr
385                 390                 395                 400

Gly Phe Gln Val Asp Ala Val Pro Ala Asn Gly Gln Thr Pro Ile Gln
                405                 410                 415

Arg Thr Ile Lys Pro Asp Val Arg Ser Tyr Thr Ile Thr Gly Leu Gln
            420                 425                 430

Pro Gly Thr Asp Tyr Lys Ile Tyr Leu Tyr Thr Leu Asn Asp Asn Ala
        435                 440                 445

Arg Ser Ser Pro Val Val Ile Asp Ala Ser Thr Ala Ile Asp Ala Pro
    450                 455                 460

Ser Asn Leu Arg Phe Leu Ala Thr Thr Pro Asn Ser Leu Leu Val Ser
465                 470                 475                 480

Trp Gln Pro Pro Arg Ala Arg Ile Thr Gly Tyr Ile Ile Lys Tyr Glu
                485                 490                 495

Lys Pro Gly Ser Pro Pro Arg Glu Val Val Pro Arg Pro Arg Pro Gly
            500                 505                 510

Val Thr Glu Ala Thr Ile Thr Gly Leu Glu Pro Gly Thr Glu Tyr Thr
        515                 520                 525

Ile Tyr Val Ile Ala Leu Lys Asn Asn Gln Lys Ser Glu Pro Leu Ile
    530                 535                 540

Gly Arg Lys Lys Thr
545

<210> SEQ ID NO 13
<211> LENGTH: 574
<212> TYPE: PRT
<213> ORGANISM: Artificial Sequence
<220> FEATURE:
<223> OTHER INFORMATION: fibronectin fragment named CH-296

<400> SEQUENCE: 13

Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
        35                  40                  45

Pro Ser Asp Asn Ala Val Val Leu Thr Asn Leu Leu Pro Gly Thr Glu
    50                  55                  60

Tyr Val Val Ser Val Ser Ser Val Tyr Glu Gln His Glu Ser Thr Pro
65                  70                  75                  80
```

```
Leu Arg Gly Arg Gln Lys Thr Gly Leu Asp Ser Pro Thr Gly Ile Asp
                    85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
        115                 120                 125

Ser Gly Arg Pro Arg Glu Asp Arg Val Pro His Ser Arg Asn Ser Ile
    130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
        195                 200                 205

Tyr Arg Ile Thr Tyr Gly Glu Thr Gly Gly Asn Ser Pro Val Gln Glu
    210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
            260                 265                 270

Ile Asp Lys Pro Ser Met Ala Ile Pro Ala Pro Thr Asp Leu Lys Phe
        275                 280                 285

Thr Gln Val Thr Pro Thr Ser Leu Ser Ala Gln Trp Thr Pro Pro Asn
    290                 295                 300

Val Gln Leu Thr Gly Tyr Arg Val Arg Val Thr Pro Lys Glu Lys Thr
305                 310                 315                 320

Gly Pro Met Lys Glu Ile Asn Leu Ala Pro Asp Ser Ser Ser Val Val
                325                 330                 335

Val Ser Gly Leu Met Val Ala Thr Lys Tyr Glu Val Ser Val Tyr Ala
            340                 345                 350

Leu Lys Asp Thr Leu Thr Ser Arg Pro Ala Gln Gly Val Val Thr Thr
        355                 360                 365

Leu Glu Asn Val Ser Pro Pro Arg Arg Ala Arg Val Thr Asp Ala Thr
    370                 375                 380

Glu Thr Thr Ile Thr Ile Ser Trp Arg Thr Lys Thr Glu Thr Ile Thr
385                 390                 395                 400

Gly Phe Gln Val Asp Ala Val Pro Ala Asn Gly Gln Thr Pro Ile Gln
                405                 410                 415

Arg Thr Ile Lys Pro Asp Val Arg Ser Tyr Thr Ile Thr Gly Leu Gln
            420                 425                 430

Pro Gly Thr Asp Tyr Lys Ile Tyr Leu Tyr Thr Leu Asn Asp Asn Ala
        435                 440                 445

Arg Ser Ser Pro Val Val Ile Asp Ala Ser Thr Ala Ile Asp Ala Pro
    450                 455                 460

Ser Asn Leu Arg Phe Leu Ala Thr Thr Pro Asn Ser Leu Leu Val Ser
465                 470                 475                 480

Trp Gln Pro Pro Arg Ala Arg Ile Thr Gly Tyr Ile Ile Lys Tyr Glu
                485                 490                 495
```

```
Lys Pro Gly Ser Pro Pro Arg Glu Val Val Pro Arg Pro Arg Pro Gly
                500                 505                 510

Val Thr Glu Ala Thr Ile Thr Gly Leu Glu Pro Gly Thr Glu Tyr Thr
            515                 520                 525

Ile Tyr Val Ile Ala Leu Lys Asn Asn Gln Lys Ser Glu Pro Leu Ile
        530                 535                 540

Gly Arg Lys Lys Thr Asp Glu Leu Pro Gln Leu Val Thr Leu Pro His
545                 550                 555                 560

Pro Asn Leu His Gly Pro Glu Ile Leu Asp Val Pro Ser Thr
                565                 570

<210> SEQ ID NO 14
<211> LENGTH: 302
<212> TYPE: PRT
<213> ORGANISM: Artificial Sequence
<220> FEATURE:
<223> OTHER INFORMATION: fibronectin fragment named C-CS1

<400> SEQUENCE: 14

Pro Thr Asp Leu Arg Phe Thr Asn Ile Gly Pro Asp Thr Met Arg Val
1               5                   10                  15

Thr Trp Ala Pro Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
        35                  40                  45

Pro Ser Asp Asn Ala Val Val Leu Thr Asn Leu Leu Pro Gly Thr Glu
    50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
        115                 120                 125

Ser Gly Arg Pro Arg Glu Asp Arg Val Pro His Ser Arg Asn Ser Ile
    130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
        195                 200                 205

Tyr Arg Ile Thr Tyr Gly Glu Thr Gly Gly Asn Ser Pro Val Gln Glu
    210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
            260                 265                 270

Ile Asp Lys Pro Ser Asp Glu Leu Pro Gln Leu Val Thr Leu Pro His
        275                 280                 285
```

```
Pro Asn Leu His Gly Pro Glu Ile Leu Asp Val Pro Ser Thr
    290                 295                 300
```

<210> SEQ ID NO 15
<211> LENGTH: 367
<212> TYPE: PRT
<213> ORGANISM: Artificial Sequence
<220> FEATURE:
<223> OTHER INFORMATION: fibronectin fragment named CHV-89

<400> SEQUENCE: 15

```
Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
        35                  40                  45

Pro Ser Asp Asn Ala Val Val Leu Thr Asn Leu Leu Pro Gly Thr Glu
    50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
        115                 120                 125

Ser Gly Arg Pro Arg Glu Asp Arg Val Pro His Ser Arg Asn Ser Ile
    130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
        195                 200                 205

Tyr Arg Ile Thr Tyr Gly Glu Thr Gly Gly Asn Ser Pro Val Gln Glu
    210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
            260                 265                 270

Ile Asp Lys Pro Ser Met Asn Val Ser Pro Arg Arg Ala Arg Val
        275                 280                 285

Thr Asp Ala Thr Glu Thr Thr Ile Thr Ile Ser Trp Arg Thr Lys Thr
    290                 295                 300

Glu Thr Ile Thr Gly Phe Gln Val Asp Ala Val Pro Ala Asn Gly Gln
305                 310                 315                 320

Thr Pro Ile Gln Arg Thr Ile Lys Pro Asp Val Arg Ser Tyr Thr Ile
                325                 330                 335

Thr Gly Leu Gln Pro Gly Thr Asp Tyr Lys Ile Tyr Leu Tyr Thr Leu
            340                 345                 350
```

Asn Asp Asn Ala Arg Ser Ser Pro Val Val Ile Asp Ala Ser Thr
            355                 360                 365

<210> SEQ ID NO 16
<211> LENGTH: 368
<212> TYPE: PRT
<213> ORGANISM: Artificial Sequence
<220> FEATURE:
<223> OTHER INFORMATION: fibronectin fragment named CHV-90

<400> SEQUENCE: 16

Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
            35                  40                  45

Pro Ser Asp Asn Ala Val Val Leu Thr Asn Leu Leu Pro Gly Thr Glu
50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
            115                 120                 125

Ser Gly Arg Pro Arg Glu Asp Arg Val Pro His Ser Arg Asn Ser Ile
130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
            195                 200                 205

Tyr Arg Ile Thr Tyr Gly Glu Thr Gly Gly Asn Ser Pro Val Gln Glu
210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
            260                 265                 270

Ile Asp Lys Pro Ser Met Ala Ile Asp Ala Pro Ser Asn Leu Arg Phe
            275                 280                 285

Leu Ala Thr Thr Pro Asn Ser Leu Leu Val Ser Trp Gln Pro Pro Arg
290                 295                 300

Ala Arg Ile Thr Gly Tyr Ile Ile Lys Tyr Glu Lys Pro Gly Ser Pro
305                 310                 315                 320

Pro Arg Glu Val Val Pro Arg Pro Arg Pro Gly Val Thr Glu Ala Thr
                325                 330                 335

Ile Thr Gly Leu Glu Pro Gly Thr Glu Tyr Thr Ile Tyr Val Ile Ala
            340                 345                 350

Leu Lys Asn Asn Gln Lys Ser Glu Pro Leu Ile Gly Arg Lys Lys Thr
            355                 360                 365

<210> SEQ ID NO 17
<211> LENGTH: 370
<212> TYPE: PRT
<213> ORGANISM: Artificial Sequence
<220> FEATURE:
<223> OTHER INFORMATION: fibronectin fragment named CHV-92

<400> SEQUENCE: 17

Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
            35                  40                  45

Pro Ser Asp Asn Ala Val Val Leu Thr Asn Leu Leu Pro Gly Thr Glu
50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
            115                 120                 125

Ser Gly Arg Pro Arg Glu Asp Arg Val Pro His Ser Arg Asn Ser Ile
130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
            195                 200                 205

Tyr Arg Ile Thr Tyr Gly Glu Thr Gly Gly Asn Ser Pro Val Gln Glu
210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
            260                 265                 270

Ile Asp Lys Pro Ser Met Ala Ile Pro Ala Pro Thr Asp Leu Lys Phe
            275                 280                 285

Thr Gln Val Thr Pro Thr Ser Leu Ser Ala Gln Trp Thr Pro Pro Asn
290                 295                 300

Val Gln Leu Thr Gly Tyr Arg Val Arg Val Thr Pro Lys Glu Lys Thr
305                 310                 315                 320

Gly Pro Met Lys Glu Ile Asn Leu Ala Pro Asp Ser Ser Ser Val Val
                325                 330                 335

Val Ser Gly Leu Met Val Ala Thr Lys Tyr Glu Val Ser Val Tyr Ala
            340                 345                 350

Leu Lys Asp Thr Leu Thr Ser Arg Pro Ala Gln Gly Val Val Thr Thr
        355                 360                 365

Leu Glu
    370

<210> SEQ ID NO 18
<211> LENGTH: 457
<212> TYPE: PRT
<213> ORGANISM: Artificial Sequence
<220> FEATURE:
<223> OTHER INFORMATION: fibronectin fragment named CHV-179

<400> SEQUENCE: 18

Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
            35                  40                  45

Pro Ser Asp Asn Ala Val Val Leu Thr Asn Leu Leu Pro Gly Thr Glu
    50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
        115                 120                 125

Ser Gly Arg Pro Arg Glu Asp Arg Val Pro His Ser Arg Asn Ser Ile
    130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
        195                 200                 205

Tyr Arg Ile Thr Tyr Gly Glu Thr Gly Gly Asn Ser Pro Val Gln Glu
    210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
            260                 265                 270

Ile Asp Lys Pro Ser Met Asn Val Ser Pro Pro Arg Arg Ala Arg Val
        275                 280                 285

Thr Asp Ala Thr Glu Thr Thr Ile Thr Ile Ser Trp Arg Thr Lys Thr
    290                 295                 300

Glu Thr Ile Thr Gly Phe Gln Val Asp Ala Val Pro Ala Asn Gly Gln
305                 310                 315                 320

Thr Pro Ile Gln Arg Thr Ile Lys Pro Asp Val Arg Ser Tyr Thr Ile
                325                 330                 335

```
Thr Gly Leu Gln Pro Gly Thr Asp Tyr Lys Ile Tyr Leu Tyr Thr Leu
            340                 345                 350

Asn Asp Asn Ala Arg Ser Ser Pro Val Val Ile Asp Ala Ser Thr Ala
            355                 360                 365

Ile Asp Ala Pro Ser Asn Leu Arg Phe Leu Ala Thr Thr Pro Asn Ser
            370                 375                 380

Leu Leu Val Ser Trp Gln Pro Pro Arg Ala Arg Ile Thr Gly Tyr Ile
385                 390                 395                 400

Ile Lys Tyr Glu Lys Pro Gly Ser Pro Arg Glu Val Val Pro Arg
                405                 410                 415

Pro Arg Pro Gly Val Thr Glu Ala Thr Ile Thr Gly Leu Glu Pro Gly
            420                 425                 430

Thr Glu Tyr Thr Ile Tyr Val Ile Ala Leu Lys Asn Asn Gln Lys Ser
            435                 440                 445

Glu Pro Leu Ile Gly Arg Lys Lys Thr
            450                 455

<210> SEQ ID NO 19
<211> LENGTH: 459
<212> TYPE: PRT
<213> ORGANISM: Artificial Sequence
<220> FEATURE:
<223> OTHER INFORMATION: fibronectin fragment named CHV-181

<400> SEQUENCE: 19

Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
            35                  40                  45

Pro Ser Asp Asn Ala Val Val Leu Thr Asn Leu Leu Pro Gly Thr Glu
50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
            85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
            115                 120                 125

Ser Gly Arg Pro Arg Glu Asp Arg Val Pro His Ser Arg Asn Ser Ile
130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
            165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
            195                 200                 205

Tyr Arg Ile Thr Tyr Gly Glu Thr Gly Gly Asn Ser Pro Val Gln Glu
            210                 215                 220

Phe Thr Val Pro Gly Ser Lys Ser Thr Ala Thr Ile Ser Gly Leu Lys
225                 230                 235                 240
```

Pro Gly Val Asp Tyr Thr Ile Thr Val Tyr Ala Val Thr Gly Arg Gly
            245                 250                 255

Asp Ser Pro Ala Ser Ser Lys Pro Ile Ser Ile Asn Tyr Arg Thr Glu
        260                 265                 270

Ile Asp Lys Pro Ser Met Ala Ile Pro Ala Pro Thr Asp Leu Lys Phe
            275                 280                 285

Thr Gln Val Thr Pro Thr Ser Leu Ser Ala Gln Trp Thr Pro Pro Asn
        290                 295                 300

Val Gln Leu Thr Gly Tyr Arg Val Arg Val Thr Pro Lys Glu Lys Thr
305                 310                 315                 320

Gly Pro Met Lys Glu Ile Asn Leu Ala Pro Asp Ser Ser Ser Val Val
                325                 330                 335

Val Ser Gly Leu Met Val Ala Thr Lys Tyr Glu Val Ser Val Tyr Ala
            340                 345                 350

Leu Lys Asp Thr Leu Thr Ser Arg Pro Ala Gln Gly Val Val Thr Thr
        355                 360                 365

Leu Glu Asn Val Ser Pro Pro Arg Arg Ala Arg Val Thr Asp Ala Thr
    370                 375                 380

Glu Thr Thr Ile Thr Ile Ser Trp Arg Thr Lys Thr Glu Thr Ile Thr
385                 390                 395                 400

Gly Phe Gln Val Asp Ala Val Pro Ala Asn Gly Gln Thr Pro Ile Gln
                405                 410                 415

Arg Thr Ile Lys Pro Asp Val Arg Ser Tyr Thr Ile Thr Gly Leu Gln
            420                 425                 430

Pro Gly Thr Asp Tyr Lys Ile Tyr Leu Tyr Thr Leu Asn Asp Asn Ala
        435                 440                 445

Arg Ser Ser Pro Val Val Ile Asp Ala Ser Thr
    450                 455

<210> SEQ ID NO 20
<211> LENGTH: 276
<212> TYPE: PRT
<213> ORGANISM: Artificial Sequence
<220> FEATURE:
<223> OTHER INFORMATION: fibronectin fragment named H-275-Cys

<400> SEQUENCE: 20

Met Ala Ala Ser Ala Ile Pro Ala Pro Thr Asp Leu Lys Phe Thr Gln
1               5                   10                  15

Val Thr Pro Thr Ser Leu Ser Ala Gln Trp Thr Pro Pro Asn Val Gln
            20                  25                  30

Leu Thr Gly Tyr Arg Val Arg Val Thr Pro Lys Glu Lys Thr Gly Pro
        35                  40                  45

Met Lys Glu Ile Asn Leu Ala Pro Asp Ser Ser Ser Val Val Val Ser
    50                  55                  60

Gly Leu Met Val Ala Thr Lys Tyr Glu Val Ser Val Tyr Ala Leu Lys
65                  70                  75                  80

Asp Thr Leu Thr Ser Arg Pro Ala Gln Gly Val Val Thr Thr Leu Glu
            85                  90                  95

Asn Val Ser Pro Pro Arg Arg Ala Arg Val Thr Asp Ala Thr Glu Thr
        100                 105                 110

Thr Ile Thr Ile Ser Trp Arg Thr Lys Thr Glu Thr Ile Thr Gly Phe
    115                 120                 125

Gln Val Asp Ala Val Pro Ala Asn Gly Gln Thr Pro Ile Gln Arg Thr
    130                 135                 140

```
Ile Lys Pro Asp Val Arg Ser Tyr Thr Ile Thr Gly Leu Gln Pro Gly
145                 150                 155                 160

Thr Asp Tyr Lys Ile Tyr Leu Tyr Thr Leu Asn Asp Asn Ala Arg Ser
                165                 170                 175

Ser Pro Val Val Ile Asp Ala Ser Thr Ala Ile Asp Ala Pro Ser Asn
            180                 185                 190

Leu Arg Phe Leu Ala Thr Thr Pro Asn Ser Leu Leu Val Ser Trp Gln
        195                 200                 205

Pro Pro Arg Ala Arg Ile Thr Gly Tyr Ile Ile Lys Tyr Glu Lys Pro
    210                 215                 220

Gly Ser Pro Pro Arg Glu Val Val Pro Arg Pro Arg Pro Gly Val Thr
225                 230                 235                 240

Glu Ala Thr Ile Thr Gly Leu Glu Pro Gly Thr Glu Tyr Thr Ile Tyr
                245                 250                 255

Val Ile Ala Leu Lys Asn Asn Gln Lys Ser Glu Pro Leu Ile Gly Arg
            260                 265                 270

Lys Lys Thr Cys
        275

<210> SEQ ID NO 21
<211> LENGTH: 658
<212> TYPE: PRT
<213> ORGANISM: Artificial Sequence
<220> FEATURE:
<223> OTHER INFORMATION: fibronectin fragment named CH-296Na

<400> SEQUENCE: 21

Met Pro Thr Asp Leu Arg Phe Thr Asn Ile Gly Pro Asp Thr Met Arg
1               5                   10                  15

Val Thr Trp Ala Pro Pro Pro Ser Ile Asp Leu Thr Asn Phe Leu Val
            20                  25                  30

Arg Tyr Ser Pro Val Lys Asn Glu Glu Asp Val Ala Glu Leu Ser Ile
        35                  40                  45

Ser Pro Ser Asp Asn Ala Val Val Leu Thr Asn Leu Leu Pro Gly Thr
    50                  55                  60

Glu Tyr Val Val Ser Val Ser Ser Val Tyr Gln His Glu Ser Thr
65                  70                  75                  80

Pro Leu Arg Gly Arg Gln Lys Thr Gly Leu Asp Ser Pro Thr Gly Ile
                85                  90                  95

Asp Phe Ser Asp Ile Thr Ala Asn Ser Phe Thr Val His Trp Ile Ala
            100                 105                 110

Pro Arg Ala Thr Ile Thr Gly Tyr Arg Ile Arg His His Pro Glu His
        115                 120                 125

Phe Ser Gly Arg Pro Arg Glu Asp Arg Val Pro His Ser Arg Asn Ser
    130                 135                 140

Ile Thr Leu Thr Asn Leu Thr Pro Gly Thr Glu Tyr Val Val Ser Ile
145                 150                 155                 160

Val Ala Leu Asn Gly Arg Glu Glu Ser Pro Leu Leu Ile Gly Gln Gln
                165                 170                 175

Ser Thr Val Ser Asp Val Pro Arg Asp Leu Glu Val Val Ala Ala Thr
            180                 185                 190

Pro Thr Ser Leu Leu Ile Ser Trp Asp Ala Pro Ala Val Thr Val Arg
        195                 200                 205

Tyr Tyr Arg Ile Thr Tyr Gly Glu Thr Gly Gly Asn Ser Pro Val Gln
    210                 215                 220
```

```
Glu Phe Thr Val Pro Gly Ser Lys Ser Thr Ala Thr Ile Ser Gly Leu
225                 230                 235                 240

Lys Pro Gly Val Asp Tyr Thr Ile Thr Val Tyr Ala Val Thr Gly Arg
                245                 250                 255

Gly Asp Ser Pro Ala Ser Ser Lys Pro Ile Ser Ile Asn Tyr Arg Thr
            260                 265                 270

Glu Ile Asp Lys Pro Ser Gln Met Gln Val Thr Asp Val Gln Asp Asn
275                 280                 285

Ser Ile Ser Val Lys Trp Leu Pro Ser Ser Ser Pro Val Thr Gly Tyr
290                 295                 300

Arg Val Thr Thr Thr Pro Lys Asn Gly Pro Gly Pro Thr Lys Thr Lys
305                 310                 315                 320

Thr Ala Gly Pro Asp Gln Thr Glu Met Thr Ile Glu Gly Leu Gln Pro
                325                 330                 335

Thr Val Glu Tyr Val Val Ser Val Tyr Ala Gln Asn Pro Ser Gly Glu
                340                 345                 350

Ser Gln Pro Leu Val Gln Thr Ala Val Thr Ala Ile Pro Ala Pro Thr
            355                 360                 365

Asp Leu Lys Phe Thr Gln Val Thr Pro Thr Ser Leu Ser Ala Gln Trp
370                 375                 380

Thr Pro Pro Asn Val Gln Leu Thr Gly Tyr Arg Val Arg Val Thr Pro
385                 390                 395                 400

Lys Glu Lys Thr Gly Pro Met Lys Glu Ile Asn Leu Ala Pro Asp Ser
                405                 410                 415

Ser Ser Val Val Val Ser Gly Leu Met Val Ala Thr Lys Tyr Glu Val
                420                 425                 430

Ser Val Tyr Ala Leu Lys Asp Thr Leu Thr Ser Arg Pro Ala Gln Gly
            435                 440                 445

Val Val Thr Thr Leu Glu Asn Val Ser Pro Pro Arg Arg Ala Arg Val
450                 455                 460

Thr Asp Ala Thr Glu Thr Thr Ile Thr Ile Ser Trp Arg Thr Lys Thr
465                 470                 475                 480

Glu Thr Ile Thr Gly Phe Gln Val Asp Ala Val Pro Ala Asn Gly Gln
                485                 490                 495

Thr Pro Ile Gln Arg Thr Ile Lys Pro Asp Val Arg Ser Tyr Thr Ile
            500                 505                 510

Thr Gly Leu Gln Pro Gly Thr Asp Tyr Lys Ile Tyr Leu Tyr Thr Leu
            515                 520                 525

Asn Asp Asn Ala Arg Ser Ser Pro Val Val Ile Asp Ala Ser Thr Ala
530                 535                 540

Ile Asp Ala Pro Ser Asn Leu Arg Phe Leu Ala Thr Thr Pro Asn Ser
545                 550                 555                 560

Leu Leu Val Ser Trp Gln Pro Pro Arg Ala Arg Ile Thr Gly Tyr Ile
                565                 570                 575

Ile Lys Tyr Glu Lys Pro Gly Ser Pro Pro Arg Glu Val Val Pro Arg
            580                 585                 590

Pro Arg Pro Gly Val Thr Glu Ala Thr Ile Thr Gly Leu Glu Pro Gly
            595                 600                 605

Thr Glu Tyr Thr Ile Tyr Val Ile Ala Leu Lys Asn Asn Gln Lys Ser
610                 615                 620
```

```
Glu Pro Leu Ile Gly Arg Lys Lys Thr Asp Glu Leu Pro Gln Leu Val
625                 630             635             640

Thr Leu Pro His Pro Asn Leu His Gly Pro Glu Ile Leu Asp Val Pro
                645             650             655

Ser Thr
```

METHOD OF PRODUCING LYMPHOCYTES

TECHNICAL FIELD

The present invention relates to a method for preparing lymphocytes, which is useful in the medical field.

BACKGROUND ART

A living body is protected from foreign substances mainly by an immune response, and an immune system has been established by various cells and the soluble factors produced thereby. Among them, leukocytes, especially lymphocytes, play a key role. The lymphocytes are classified in two major types, B lymphocyte (which may be hereinafter referred to as B cell) and T lymphocyte (which may be hereinafter referred to as T cell), both of which specifically recognize an antigen and act on the antigen to protect the living body.

T cell is subclassified to helper T cell having CD (Cluster of Differentiation)4 marker (which may be hereinafter referred to as $T_H$), mainly involved in assisting in antibody production and induction of various immune responses, and cytotoxic T cell having CD8 marker ($T_c$: cytotoxic T lymphocyte, also referred to as killer T cell, which may be hereinafter referred to as CTL), mainly exhibiting a cytotoxic activity. CTL, which plays the most important role in recognizing, destroying and eliminating tumor cell, virus-infected cell or the like, does not produce an antibody specifically reacting with an antigen like B cell, but directly recognizes and acts on antigens (antigenic peptide) from a target cell which is associated with major histocompatibility complex [MHC, which may be also referred to as human leukocyte antigen (HLA) in human] Class I molecules existing on the surface of the target cell membrane. At this time, T cell receptor (hereinafter referred to as TCR) existing on the surface of the CTL membrane specifically recognizes the above-mentioned antigenic peptides and MHC Class I molecules, and determines whether the antigenic peptide is autologous or nonautologous. Target cell which has been determined to be nonautologous is then specifically destroyed and eliminated by CTL.

Recent years, a therapy which would cause a heavy physical burden on a patient, such as pharmacotherapy and radiotherapy, has been reconsidered, and an interest has increased in an immunotherapy with a light physical burden on a patient. Especially, there has been remarked an effectiveness of adoptive immunotherapy in which a lymphocyte such as CTL that specifically reacts with an antigen of interest is induced ex vivo from a lymphocyte derived from a human, or the above-mentioned lymphocyte is expanded without induction, and then transferred to a patient. For example, it has been suggested in an animal model that adoptive immunotherapy is an effective therapy for virus infection and tumor (for example, Non-Patent Publications 1 and 2). In this therapy, it is important to maintain or increase the number of the CTLs in a state in which the antigen-specific cytotoxic activity of the cells is maintained or enhanced.

In the adoptive immunotherapy as described above, it is necessary to administer cytotoxic lymphocytes in the number of cells of a given amount or larger in order to obtain a therapeutic effect. In other words, it can be said that it is the greatest problem to obtain the above number of cells ex vivo in a short period of time.

In order to maintain and enhance an antigen-specific cytotoxic activity of CTL, there has been generally employed a method of repeating stimulation with an antigen of interest when a specific response to an antigen for CTL is induced. However, in this method, the number of CTL finally obtained may usually be decreased, so that a sufficient number of cells cannot be obtained.

Next, regarding the preparation of the antigen-specific CTL, there has been each reported a method for isolating and expanding a CMV-specific CTL clone using autologous CMV infected fibroblast and IL-2 (for example, Non-Patent Publication 6) or using anti-CD3 monoclonal antibody (anti-CD3 mAb) and IL-2 (for example, Non-Patent Publication 7).

Furthermore, Patent Publication 1 discloses an REM method (rapid expansion method). This REM method is a method for expanding a primary T cell population containing antigen-specific CTLs and $T_H$ in a short period of time. In other words, this method is characterized in that a large amount of T cell can be provided by expanding individual T cell clones, and that the number of antigen-specific CTLs is increased using an anti-CD3 antibody, IL-2, and PBMCs (peripheral blood mononuclear cells) made deficient in an ability for expansion by irradiation, and Epstein-Barr virus (hereinafter abbreviated as EBV)-infected cells.

In addition, Patent Publication 2 discloses a modified REM method, wherein the method is a method using as feeder cells a nondividing mammal cell strain expressing a T-cell stimulating component which is distinguishable from PBMCs to reduce an amount of PBMCs used.

As lymphocytes which are effective for the treatment of a disease other than CTLs, there has been known, for example, lymphokine-activated cells (for example, Non-Patent Publication 3) and tumor-infiltrating lymphocytes (TILs) induced with interleukin-2 (IL-2) in a high concentration (for example, Non-Patent Publications 4 and 5).

The lymphokine-activated cells are a functional cell population having a cytotoxic activity, which are obtained by adding IL-2 to peripheral blood (peripheral blood leukocyte), umbilical cord blood, tissue fluid or the like containing lymphocytes, and culturing the cells in vitro for several days. In the step of culturing the lymphokine-activated cells, proliferation of the lymphokine-activated cells is further accelerated by adding an anti-CD3 antibody thereto. Further, it has been known that, in the culture step, a proliferation ratio of the cells is further improved by adding not only the anti-CD3 antibody but also an anti-CD28 antibody thereto to co-stimulate the cells (for example, Non-Patent Publication 8). The lymphokine-activated cells thus obtained have a cytotoxic activity non-specifically to various cancer cells and other targets.

Fibronectin is a gigantic glycoprotein having a molecular weight of 250 thousands, which exists in an animal blood, on the surface of a cultured cell, or in an extracellular matrix of a tissue, and has been known to have various functions. A domain structure thereof is divided into seven portions (FIG. 1 et seq), wherein three kinds of similar sequences are contained in an amino acid sequence thereof, repetitions of each of these sequences constituting the entire sequence. Three kinds of the similar sequences are referred to as type I, type II and type III. Among them, the type III is constituted by 71 to 96 amino acid residues, wherein an identity of these amino acid residues is 17 to 40%. In fibronectin, there are fourteen type III sequences, among which the 8th, 9th or 10th sequence (each being hereinafter referred to as III-8, III-9 or III-10) is contained in a cell binding domain, and the 12th, 13th or 14th sequence (each being hereinafter referred to as III-12, III-13 or III-14) is contained in a heparin binding domain. In addition, a VLA (very late activation antigen)-5 binding region is contained in III-10, and its core sequence is RGDS. In addition, a region referred to as IIICS exists at a C-terminal side of the heparin binding domain. A region referred to as CS-1 consisting of 25 amino acids and having a binding activity to VLA-4 exists in IIICS (for example, Non-Patent Publications 9 to 11).

In the preparation of the lymphokine-activated cells and the cytotoxic lymphocytes, an action of improving a proliferation ratio of the cells and an action of maintaining a cytotoxic activity by using fibronectin and a fragment thereof have been already studied by the present inventors (for example, Patent Publications 3, 4 and 5). However, considering the actual use for adoptive immunotherapy, the methods of the above-mentioned publications are not satisfactory at all, and a method for expanding lymphocytes with a further higher proliferation ratio of the cells has been desired.

Non-Patent Publication 1: authored by Greenberg, P. D., published in 1992, Advances in Immunology
Non-Patent Publication 2: Reusser P. and three others, Blood, 1991, 78(5), 1373-1380
Non-Patent Publication 3: Riddell S. A. and four others, J. Immunol., 1991, 146(8), 2795-2804
Non-Patent Publication 4: Riddell S. R. and one other, J. Immunol. Methods, 1990, 128(2), 189-201
Non-Patent Publication 5: Rosenberg S. A. et al., N. Engl. J. Med. 1987, 316(15), 889-897
Non-Patent Publication 6: Rosenberg S. A. et al., N. Engl. J. Med., 1988, 319(25), 1676-1680
Non-Patent Publication 7: Ho M. and nine others, Blood, 1993, 81(8), 2093-2101
Non-Patent Publication 8: Koberda J. and two others, J. Cancer Res. Clin. Oncol., 1993, 119(3), 131-136
Non-Patent Publication 9: authored by Deane F. Mosher, published in 1988, FIBRONECTIN, ACADEMIC PRESS INC., 1-24
Non-Patent Publication 10: Kimizuka F. and eight others, J. Biochem., 1991, 110(2), 284-291
Non-Patent Publication 11: Hanenberg H. and five others, Human Gene Therapy, 1997, 8(18), 2193-2206
Patent Publication 1: WO 96/06929
Patent Publication 2: WO 97/32970
Patent Publication 3: WO 03/016511
Patent Publication 4: WO 03/080817
Patent Publication 5: WO 2005/019450

DISCLOSURE OF THE INVENTION

Problems to be Solved by the Invention

An object of the present invention is to provide an effective method for preparing lymphocytes, which is suitably used in the medical field.

Means to Solve the Problems

A first invention of the present invention relates to a method for preparing lymphocytes characterized in that the method comprises the step of carrying out expansion in the presence of (a) fibronectin, a fragment thereof or a mixture thereof, (b) a CD3 ligand, and (c) a CD28 ligand. In the first invention of the present invention, the CD3 ligand is exemplified by an anti-CD3 antibody, and the CD28 ligand is exemplified by an anti-CD28 antibody. In addition, the fibronectin fragment is exemplified by a polypeptide (m) comprising at least any one of the amino acid sequences shown in SEQ ID NOs: 1 to 8 of Sequence Listing, or a polypeptide (n) comprising at least one amino acid sequence having substitution, deletion, insertion or addition of one or the plural number of amino acids in any one of the above-mentioned amino acid sequences, wherein the polypeptide (n) has a function equivalent to that of the above-mentioned polypeptide (m). In addition, the fibronectin fragment is exemplified by those which have a cell adhesion activity and/or a heparin binding activity. The fibronectin fragment is also exemplified by at least one polypeptide selected from the group consisting of polypeptides having any one of the amino acid sequences shown in SEQ ID NOs: 9 to 21 of Sequence Listing. In addition, in the first invention of the present invention, the lymphocytes are exemplified by lymphokine-activated cells. Moreover, in the first invention of the present invention, a method for preparing lymphocytes further comprising the step of transducing a foreign gene into lymphocytes is provided. A method for transducing the foreign gene is exemplified by a transduction method using retrovirus, adenovirus, adeno-associated virus, lentivirus or simian virus.

A second invention of the present invention relates to lymphocytes obtained by the first invention of the present invention. In addition, a third invention of the present invention relates to a medicament comprising the second invention of the present invention as an effective ingredient.

A fourth invention of the present invention relates to a method for preparing a solid phase to which at least one selected from the group consisting of an anti-CD3 antibody, an anti-CD28 antibody, fibronectin and a fragment thereof is immobilized, characterized in that the solid phase is contacted with at least one selected from the group consisting of an anti-CD3 antibody, an anti-CD28 antibody, fibronectin and a fragment thereof under an acidic condition. In the fourth invention of the present invention, the solid phase is exemplified by a cell culture carrier.

A fifth invention of the present invention relates to a solid phase to which (a) fibronectin, a fragment thereof or a mixture thereof, (b) a CD3 ligand, and (c) a CD28 ligand are immobilized. In the fifth invention of the present invention, the solid phase is exemplified by a cell culture plate, a petri dish, a flask, a bag, beads, a membrane or a slide glass.

Effects of the Invention

According to the present invention, there is provided an effective method for preparing lymphocytes. The preparation method has a high proliferation ratio of cells and is a very useful method. The lymphocytes obtained by the present invention are suitably used, for example, in adoptive immunotherapy. Therefore, there is expected a great contribution of the lymphocytes of the present invention to the medical field.

BEST MODE FOR CARRYING OUT THE INVENTION

The present invention has been completed by the findings that, by comprising the step of carrying out expansion of lymphocytes in the presence of (a) fibronectin, a fragment thereof or a mixture thereof, (b) a CD3 ligand, and (c) a CD28 ligand, a proliferation ratio of cells is highly increased.

Incidentally, the preparation of lymphocytes as used herein refers to procedures encompassing the step of expansion of the cells. The preparation of lymphocytes of the present invention is also referred to as culture of lymphocytes.

The present invention will be concretely explained hereinbelow.

(1) Fibronectin and Fragment Thereof Used in the Present Invention

The fibronectin and a fragment thereof described herein may be either those obtained from nature, or those artificially synthesized. The fibronectin and a fragment thereof can be prepared in a substantially pure form from a substance of natural origin, on the basis of the disclosure, for example, of Ruoslahti E., et al. [*J. Biol. Chem.*, 256(14), 7277-7281 (1981)]. The term "substantially pure fibronectin or fibronectin fragment" described herein means that these fibronectin and fibronectin fragment do not essentially contain other proteins existing together with fibronectin in nature. Each of the above-mentioned fibronectin and a fragment thereof can be used in the present invention alone or in admixture of plural kinds.

Here, it is known that there are a large number of splicing variants of fibronectin. As the fibronectin used in the present invention, any variant can be used so long as the desired effects of the present invention are exhibited. For example, in the case of fibronectin derived from plasma, it is known that a region referred to as ED-B present in upstream of a cell binding domain and a region referred to as ED-A present between the cell binding domain and the heparin binding domain are deleted. Such fibronectin derived from plasma can also be used in the present invention.

The useful information relating to the fibronectin fragments which can be used in the present invention and the preparation of the fragments can be obtained from Kimizuka F., et al. [*J. Biochem.*, 110, 284-291 (1991)], Kornbrihtt A. R., et al. [*EMBO J*, 4(7), 1755-1759 (1985)], Sekiguchi K., et al. [*Biochemistry*, 25(17), 4936-4941 (1986)], and the like. In addition, the nucleic acid sequence encoding fibronectin or the amino acid sequence of fibronectin is disclosed in Genbank Accession No. NM_002026 and NP_002017.

In the present invention, the fibronectin fragment is exemplified by, for example, a polypeptide (m) comprising at least one amino acid sequence comprising any of the regions of III-8 (amino acid sequence shown in SEQ ID NO: 1 of Sequence Listing), III-9 (amino acid sequence shown in SEQ ID NO: 2 of Sequence Listing), III-10 (amino acid sequence shown in SEQ ID NO: 3 of Sequence Listing), III-11 (amino acid sequence shown in SEQ ID NO: 4 of Sequence Listing), III-12 (amino acid sequence shown in SEQ ID NO: 5 of Sequence Listing), III-13 (amino acid sequence shown in SEQ ID NO: 6 of Sequence Listing), III-14 (amino acid sequence shown in SEQ ID NO: 7 of Sequence Listing), and CS-1 (amino acid sequence shown in SEQ ID NO: 8 of Sequence Listing) (see FIG. 1), and a polypeptide (n) comprising at least one amino acid sequence having substitution, deletion, insertion or addition of one or the plural number of amino acids in any of the amino acid sequences described above, wherein the polypeptide (n) has a function equivalent to that of the above-mentioned polypeptide (m). The length of the fragment is, for example, preferably from 20 to 1000, and more preferably from 100 to 800, by the number of amino acids. Here, the plural number herein is a concept that includes the several number, and is preferably from 2 to 12, more preferably from 2 to 10, and further more preferably from 2 to 8. The same can be said for the plural number hereinafter.

In addition, as the fragment, a fragment having a cell adhesion activity and/or a heparin binding activity can be preferably used. The cell adhesion activity can be evaluated by assaying binding of the fragment (its cell binding domain) used in the present invention to a cell using a known method. For example, the method as mentioned above includes a method of Williams D. A., et al. [*Nature*, 352, 438-441 (1991)]. The method is a method of determining the binding of a cell to a fragment immobilized to a culture plate. In addition, the heparin binding activity can be evaluated by assaying binding of the fragment (its heparin binding domain) used in the present invention to heparin using a known method. For example, the binding of the fragment to heparin can be evaluated in the same manner by using heparin, for example, a labeled heparin in place of the cell in the above-mentioned method of Williams D. A., et al.

Further, the fibronectin fragment is exemplified by a polypeptide selected from the group consisting of C-274 (amino acid sequence shown in SEQ ID NO: 9 of Sequence Listing), H-271 (amino acid sequence shown in SEQ ID NO: 10 of Sequence Listing), H-296 (amino acid sequence shown in SEQ ID NO: 11 of Sequence Listing), CH-271 (amino acid sequence shown in SEQ ID NO: 12 of Sequence Listing), CH-296 (amino acid sequence shown in SEQ ID NO: 13 of Sequence Listing), C-CS1 (amino acid sequence shown in SEQ ID NO: 14 of Sequence Listing), and CH-296Na (amino acid sequence shown in SEQ ID NO: 21 of Sequence Listing).

Each of the above-mentioned fragments CH-271, CH-296, CH-296Na, C-274 and C-CS1 is a polypeptide having a cell binding domain with a binding activity to VLA-5. Also, C-CS1, H-296, CH-296 and CH-296Na are polypeptides having CS-1 with a binding activity to VLA-4. Further, H-271, H-296, CH-271, CH-296 and CH-296Na are polypeptides having a heparin binding domain. Here, CH-296Na is a polypeptide comprising a region from the cell binding domain to CS-1 of fibronectin derived from plasma.

In the present invention, a fragment in which each of the above domains is modified can also be used. The heparin binding domain of the fibronectin is constituted by three type III sequences (III-12, III-13 and III-14). A fragment containing a heparin binding domain having deletion of one or two of the above type III sequences can also be used in the present invention. For example, the fragments may be exemplified by CHV-89 (amino acid sequence shown in SEQ ID NO: 15 of Sequence Listing), CHV-90 (amino acid sequence shown in SEQ ID NO: 16 of Sequence Listing) and CHV-92 (amino acid sequence shown in SEQ ID NO: 17 of Sequence Listing), which are fragments in which a cell binding site of the fibronectin (VLA-5 binding domain: Pro1239 to Ser1515) and one of the III type sequences are bound, or CHV-179 (amino acid sequence shown in SEQ ID NO: 18 of Sequence Listing) and CHV-181 (amino acid sequence shown in SEQ ID NO: 19 of Sequence Listing), which are fragments in which the cell binding site of the fibronectin and two of the type III sequences are bound. CHV-89, CHV-90 and CHV-92 contain III-13, III-14 and III-12, respectively, and CHV-179 contains III-13 and III-14, and CHV-181 contains III-12 and III-13, respectively.

In addition, a fragment having addition of an additional amino acid to each of the above-mentioned fragments can be used in the present invention. For example, the fragment can be prepared by adding a desired amino acid to each of the above-mentioned fragments. For example, H-275-Cys (amino acid sequence shown in SEQ ID NO: 20 of Sequence Listing) is a fragment having a heparin binding domain of the fibronectin, and cysteine residue at a C-terminal.

The fragment used in the present invention may be those comprising a polypeptide comprising an amino acid sequence having substitution, deletion, insertion or addition of one or the plural number of amino acids in an amino acid sequence of a polypeptide constituting the fragment at least partially containing an amino acid sequence of naturally occurring fibronectin exemplified above, wherein the polypeptide has a function equivalent to that of the fragment, so long as the desired effects of the present invention are obtained.

It is preferable that the substitution or the like of the amino acids is carried out to an extent that it can change physicochemical characteristics and the like of a polypeptide within the range that the inherent function of the polypeptide can be maintained. For example, it is preferable that the substitution or the like of the amino acids is conservative, within the range that the characteristics inherently owned by the polypeptide (for example, hydrophobicity, hydrophilicity, electric charge, pK and the like) are not substantially changed. For example, it is preferable that the substitution of the amino acids is substitutions within each of the groups of: 1. glycine, alanine; 2. valine, isoleucine, leucine; 3. aspartic acid, glutamic acid, asparagine, glutamine; 4. serine, threonine; 5. lysine, arginine; 6. phenylalanine, tyrosine, and that deletion, addition or insertion of amino acids is deletion, addition or insertion in the amino acids having characteristics similar to the characteristics of the surroundings of the subject site in the polypeptide within the range that the characteristics of the surroundings of the subject site are not substantially changed.

Here, when the fragment used in the present invention has been obtained by genetic engineering technique, in a case where, for example, the polypeptide is prepared using *Escherichia coli* or the like as a host, methionine at a N-terminal is sometimes deleted by the effect of methionine peptidase derived from *Escherichia coli* or the like, and the polypeptide as mentioned above can be also used in the present invention. In other words, polypeptides of which methionine at a N-terminal is deleted from the polypeptides recited in SEQ ID NOs: 20 and 21 of Sequence Listing can be also preferably used in the present invention.

The substitution or the like of the amino acids may be those naturally occurring being caused by difference between species or individuals, or may be those artificially induced. Artificial induction may be carried out by a known method and is not particularly limited. For example, in accordance with a known method, a given nucleic acid having substitution, deletion, addition or insertion of one or the plural number of nucleotides in the nucleic acid encoding the above-mentioned region and the given fragment derived from naturally occurring fibronectin is prepared, and the nucleic acid is used, whereby a polypeptide comprising an amino acid sequence having substitution or the like in the amino acid sequence of the polypeptide constituting the fragments and the like, having a function equivalent to that of the above-mentioned region and the given fragment derived from naturally occurring fibronectin can be prepared.

In addition, the phrase "having a function equivalent" herein refers to that the polypeptide, which is a comparative control, has an action of improving expansion fold of lymphocytes which is possessed by the fibronectin fragment. The above-mentioned action can be appropriately confirmed in accordance with the method described in Example 1 set forth below. In addition, as the fragment comprising a polypeptide having the substitution or the like of the amino acids, a fragment having a cell adhesion activity and/or a heparin binding activity is preferred. The cell adhesion activity and the heparin binding activity can be evaluated in accordance with the above-mentioned methods for determining those activities.

As the fragment comprising a polypeptide having the substitution or the like of the amino acids, for example, a fragment having one or more amino acids inserted as a linker between two different domains can also be used in the present invention.

Incidentally, as the fibronectin, similarly to the above-mentioned fragment, there can be used in the present invention a polypeptide having an amino acid sequence having substitution, deletion, insertion or addition of one or the plural number of amino acids in an amino acid sequence constituting the polypeptide of the fibronectin, wherein the polypeptide has the action of improving expansion fold of lymphocytes.

In addition, as the fibronectin or the fragment thereof used in the present invention, so long as the desired effects of the present invention are obtained, there can be used a polypeptide having the homology of 50% or more, preferably a polypeptide having the homology of 70% or more, more preferably a polypeptide having the homology of 90% or more, and further more preferably a peptide having the homology of 95% or more, to an amino acid sequence of a polypeptide constituting the fibronectin or the fragment thereof, wherein the polypeptide constituting the fibronectin or the fragment thereof has a function equivalent to that of the naturally occurring fibronectin or the fragment at least partially containing an amino acid sequence thereof exemplified above. Incidentally, for example, DNASIS Pro Ver.2.6 (manufactured by TAKARA BID INC.) can be used for a calculation of the homology.

The fibronectin fragment described herein can be also prepared as a recombinant fibronectin fragment from a genetic recombinant on the basis of, for example, the description of the specification of U.S. Pat. No. 5,198,423. For example, each of the above-mentioned fragments of H-271 (SEQ ID NO: 10), H-296 (SEQ ID NO: 11), CH-271 (SEQ ID NO: 12) and CH-296 (SEQ ID NO: 13) and a method of obtaining these fragments are described in detail in the specification of this patent. In addition, CH-296Na (SEQ ID NO: 21) and the preparation method thereof are described in WO 2005/019450. In addition, the above-mentioned C-274 (SEQ ID NO: 9) fragment can be obtained in accordance with the method described in the specification of U.S. Pat. No. 5,102,988. Further, the C-CS1 (SEQ ID NO: 14) fragment can be obtained in accordance with the method described in the specification of Japanese Patent Gazette No. 3104178. Each of the above-mentioned fragment of CHV-89 (SEQ ID NO: 15), CHV-90 (SEQ ID NO: 16) or CHV-179 (SEQ ID NO: 18) can be obtained in accordance with the method described in the specification of Japanese Patent Gazette No. 2729712. In addition, the CHV-181 (SEQ ID NO: 19) fragment can be obtained in accordance with the method described in WO 97/18318. The CHV-92 (SEQ ID NO: 17) fragment can be obtained by genetic engineering technique using a plasmid constructed in a usual manner on the basis of the plasmid described in the literatures by referring to the specification of Japanese Patent Gazette No. 2729712 and WO 97/18318.

These fragments or fragments which can be derived from these fragments in a usual manner can be prepared by using microorganisms deposited to the International Patent Organism Depositary, National Institute of Advanced Industrial Science and Technology, Tsukuba Central 6, 1-1, Higashi 1-chome, Tsukuba-shi, Ibaraki-ken, Japan (Zip code 305-8566) under the following accession numbers, or also prepared by modifying a plasmid carried in each microorganism in accordance with a known method.

1. *Escherichia coli* HB101/pHD101
FERM BP-2264 (*Escherichia coli* carrying a plasmid encoding H-271, Date of Deposit: Jan. 30, 1989);
2. *Escherichia coli* HB101/pCH102
FERM BP-2800 (*Escherichia coli* carrying a plasmid encoding CH-296, Date of Deposit: May 12, 1989);
3. *Escherichia coli* HB101/pCH101
FERM BP-2799 (*Escherichia coli* carrying a plasmid encoding CH-271, Date of Deposit: May 12, 1989);
4. *Escherichia coli* HB101/pHD102
FERM BP-7420 (*Escherichia coli* carrying a plasmid encoding H-296, Date of Deposit: May 12, 1989);
5. *Escherichia coli* JM109/pTF7221
FERM BP-1915 (*Escherichia coli* carrying a plasmid encoding C-274, Date of Deposit: Jun. 17, 1988);

6. *Escherichia coli* HB101/pCS25
FERM BP-5723 (*Escherichia coli* carrying a plasmid encoding C-CS1, Date of Deposit: Mar. 5, 1990);
7. pCold14-CH296Na
FERM BP-10073 (a plasmid encoding CH-296Na, Date of Deposit: Jul. 23, 2004);
8. *Escherichia coli* HB101/pCHV89
FERM P-12182 (*Escherichia coli* carrying a plasmid encoding CHV-89, Date of Deposit: Apr. 8, 1991); and
9. *Escherichia coli* HB101/pCHV179
FERM P-12183 (*Escherichia coli* carrying a plasmid encoding CHV-179, Date of Deposit: Apr. 8, 1991).

Since the fibronectin is a gigantic glycoprotein, it is not necessarily easy industrially and in the preparation of the medicament to prepare and use a naturally occurring protein. In addition, since the fibronectin is a multifunctional protein, there may be considered some disadvantages caused by a region different from the region exhibiting the effect by the method of the present invention depending on the conditions of its use. For these reasons, it is preferable to use preferably a fibronectin fragment and more preferably a recombinant fibronectin fragment obtained as described above, in the present invention, from the viewpoint of availability, easy handling, and safety. In addition, the molecular weight of the fibronectin fragment used in the present invention is not particularly limited, and is preferably from 1 to 200 kD, more preferably from 5 to 190 kD, and even more preferably from 10 to 180 kD. The molecular weight can be determined, for example, by SDS-polyacrylamide gel electrophoresis.

Here, in the amino acid sequence of the polypeptide constituting the fibronectin fragment of the present invention, the part of amino acid sequence other than the amino acid sequence of the polypeptide constituting a naturally occurring fibronectin fragment is arbitrary and is not specifically limited, so long as the exhibition of the desired effects of the present invention is not inhibited.

(2) Method for Preparing Lymphocytes

The method for preparing lymphocytes of the present invention will be concretely explained below. The method of the present invention is a method for preparing lymphocytes characterized in that the method comprises the step of carrying out expansion of lymphocytes in the presence of (a) the above-mentioned fibronectin, a fragment thereof or a mixture thereof, (b) a CD3 ligand, and (c) a CD28 ligand. Hereinafter, (a) the above-mentioned fibronectin, a fragment thereof or a mixture thereof, (b) a CD3 ligand, and (c) a CD28 ligand described above may be referred to as the effective ingredients of the present invention.

The "lymphocytes" as used herein means a group of cells containing a lymphocyte. In the method for preparing lymphocytes of the present invention, the kind of cells subjected to the method, conditions for culture and the like are appropriately adjusted, whereby, for example, expansion of the lymphocytes is carried out ex vivo.

The lymphocytes obtained by the method of the present invention are not particularly limited, and include, for example, a cell population containing at least one kind of cells of lymphokine-activated cells, cytotoxic T cells (CTLs), tumor-infiltrating lymphocytes (TILs), NK cells, naive cells, memory cells, and the like, or the like. Incidentally, the lymphokine-activated cells herein refer to a functional cell population having a cytotoxic activity, which is obtained by adding IL-2 to peripheral blood (peripheral blood leukocyte), umbilical cord blood, tissue fluid or the like containing lymphocytes, and culturing the cells in vitro for several days. The above-mentioned cell population may be generally referred to as the lymphokine-activated killer cells (LAK cells). Since the cell population also contains a cell which doesn't have a cytotoxicity, the cell population is referred to as the lymphokine-activated cells in the specification of the present application.

In the present invention, the cells used for preparing lymphocytes are exemplified by peripheral blood mononuclear cells (PBMCs), NK cells, naive cells, memory cells, hemopoietic stem cells, umbilical cord blood mononuclear cells, and the like. In addition, so long as a cell is a hemocyte, the cell can be used in the present invention. Any of these cells which are collected from a living body can be used, or which are obtained by culture can be used directly or those which are subjected to frozen storage can be used. Incidentally, in the method for preparing lymphocytes of the present invention, a material containing the above-mentioned cells, for example, a blood such as peripheral blood or umbilical cord blood; one obtained by removing components such as erythrocyte and plasma from the blood; a marrow fluid and the like can be used. Further, when CTLs are prepared according to the method of the present invention, CTLs induced by giving stimulation with an antigen to the cells as mentioned above and CTLs derived from a living body can be also used.

The method for preparing lymphocytes of the present invention is a method for preparing lymphocytes comprising the step of carrying out expansion in the presence of the effective ingredients of the present invention. The culture is carried out during the entire period of culture of the lymphocytes, or during any part of the period. In other words, the present invention encompasses those embodiments which comprise the above-mentioned step in a part of the steps of preparing lymphocytes.

In the present invention, a CD3 ligand is not particularly limited, so long as a substance has a binding activity to CD3, and is exemplified by, for example, an anti-CD3 antibody, preferably by an anti-CD3 monoclonal antibody, and particularly preferably by okt3. The concentration of a CD3 ligand in the culture solution is not particularly limited. For example, in a case where the anti-CD3 monoclonal antibody is used, the concentration is, for example, preferably from 0.001 to 100 μg/mL, and more preferably from 0.01 to 100 μg/mL.

In addition, in the present invention, a CD28 ligand is not particularly limited, so long as a substance has a binding activity to CD28, and is exemplified by, for example, an anti-CD28 antibody, B7-1, B7-2, and CD80, and particularly preferably by an anti-CD28 monoclonal antibody. The concentration of a CD28 ligand in the culture solution is not particularly limited. For example, in a case where the anti-CD28 monoclonal antibody is used, the concentration is, for example, preferably from 0.001 to 100 μg/mL, and more preferably from 0.01 to 100 μg/mL.

In the present invention, the concentration of fibronectin, a fragment thereof or a mixture thereof in the culture solution is not particularly limited, and is, for example, preferably from 0.001 to 500 μg/mL, and more preferably from 0.01 to 500 μg/mL.

The medium used in the method for preparing lymphocytes of the present invention is not particularly limited, and a known medium prepared by mixing components necessary for expanding lymphocytes can be used. For example, a commercially available medium can be appropriately selected to be used. These media may contain appropriate proteins, cytokines and other components in addition to the inherent constituents. Preferably, a medium containing IL-2 is used in the present invention. The concentration of IL-2 in the medium is not particularly limited, and is, for example, preferably from 0.01 to $1 \times 10^5$ U/mL, and more preferably from 0.1 to $1 \times 10^4$ U/mL. Also, besides the above, a lymphocyte-stimulating factor such as lectin can be added. The concentration of the component in a medium is not particularly limited, so long as the desired effects can be obtained.

Furthermore, in expansion of lymphocytes, serum and plasma can be also added to a medium. The amount of serum and plasma added to a medium is not particularly limited, and is exemplified by from 0% by volume to 20% by volume. Incidentally, as described in WO 2005/019450, the present inventors have found that the preparation of lymphocytes maintaining a high expansion fold can be carried out even though the total concentration of serum and plasma contained in a medium is at a low concentration of 0% by volume or more and less than 5% by volume, by carrying out the preparation of lymphocytes in the presence of fibronectin, a fragment thereof or a mixture thereof. In other words, similarly in the present invention, the total concentration of serum and plasma contained in a medium is preferably 0% by volume or more and less than 5% by volume, from the viewpoint of safety or amelioration of burden on a patient, and the present invention is not limited thereto. Incidentally, origin of the serum or plasma may be any of autologous (meaning that the origin is the same as that of the lymphocytes cultured) serum or plasma or nonautologous (meaning that the origin is different from that of the lymphocytes cultured) serum or plasma. Preferably, autologous serum or plasma can be used, from the viewpoint of safety. Here, the total concentration of serum and/or plasma contained of 0% by volume means that serum and plasma are not added to a medium.

In the method of the present invention, the preparation of lymphocytes, i.e., the expansion of lymphocytes is usually carried out in a medium containing given components in the presence of the above-mentioned effective ingredients of the present invention. The number of cells at the initiation of culture used in the present invention is not particularly limited. For example, the number of cells is exemplified by, for example, from 1 cell/mL to $1\times10^8$ cells/mL, preferably from 1 cell/mL to $5\times10^7$ cells/mL, and more preferably from 1 cell/mL to $2\times10^7$ cells/mL. In addition, the culture conditions are not particularly limited, and usual conditions used for cell culture can be employed. For example, cells can be cultured under the conditions of 37° C. in the presence of 5% $CO_2$ and the like. In addition, the medium can be diluted by adding a fresh medium to the cell culture solution, the medium can be exchanged, or the cell culture equipment can be exchanged at appropriate intervals.

As the cell culture equipment used in the method for preparing lymphocytes of the present invention, for example, without particular limitation, a cell culture plate, a petri dish, a flask, a bag, a large culture bath, a bioreactor and the like can be used. Here, as a bag, a $CO_2$ gas-permeable bag for cell culture can be used. In addition, upon industrial preparation of a large amount of lymphocytes, a large culture bath can be used. Furthermore, the culture can be carried out in either open system or closed system. Preferably, the culture is carried out in closed system, from the viewpoint of safety of the resulting lymphocytes.

Besides the coexistence of (a) fibronectin, a fragment thereof or a mixture thereof, (b) a CD3 ligand, and (c) a CD28 ligand used in the present invention, by dissolving the components in a medium, there may be used by immobilization to an appropriate solid phase, for example, a cell culture equipment (including any of those of open system and closed system), such as a cell culture plate, a petri dish, a flask or a bag, or to a cell culture carrier such as beads, a membrane or a slide glass. The materials for those solid phases are not particularly limited so long as the materials can be used for cell culture. When the components are immobilized to, for example, the above-mentioned equipment, it is preferable to immobilize a given amount of each component on the amount of the medium to be placed in the equipment so that the medium has a similar proportion to a desired concentration of the case where the components are used by dissolving the components in a medium upon placing the medium in the equipment. The amount of the components immobilized is not particularly limited, so long as the desired effects can be obtained. The above-mentioned carrier is used by immersing the carrier in a culture solution in the cell culture equipment during the cell culture. When the above-mentioned components are immobilized to the above-mentioned carrier, it is preferable to immobilize a given amount of each component on the amount of the medium to be placed in the equipment so that the medium has a similar proportion to a desired concentration of the case where the components are used by dissolving the components in a medium upon placing the carrier in the medium. The amount of the components immobilized is not particularly limited, so long as the desired effects can be obtained.

In addition, in another embodiment of the present invention, there is provided a solid phase to which (a) fibronectin, a fragment thereof or a mixture thereof, (b) a CD3 ligand, and (c) a CD28 ligand are immobilized. The solid phase is exemplified by the above-mentioned solid phase, and preferably a cell culture plate, a petri dish, a flask, a bag, beads, a membrane, a slide glass, and the like. The amount of the above (a) to (c) immobilized to the solid phase is not particularly limited, so long as the desired effects can be obtained upon using the solid phase for the method for preparing lymphocytes of the present invention. For example, the amount can be appropriately determined as desired, according to the amount of the effective ingredients or the like contained in the above-mentioned medium used in the method of the present invention. Also, as an immobilization method of the above (a) to (c), it is preferable to carry out the immobilization preferably under an acidic condition set forth below, from the viewpoint of improvement in immobilization efficiency.

When an anti-CD3 antibody and an anti-CD28 antibody are used as the CD3 ligand and the CD28 ligand, a method for immobilizing these antibodies, fibronectin, or a fragment thereof to the solid phase is not particularly limited. For example, these antibodies, fibronectin, or a fragment thereof can be immobilized by being contacted with the solid phase in an appropriate buffer solution. Especially preferably, as described in Examples 2 and 3 set forth below, the immobilization is carried out under an acidic condition, whereby the immobilization of these antibodies, fibronectin, or a fragment thereof can be more effectively carried out. Incidentally, carrying out the immobilization of these antibodies, fibronectin, or a fragment thereof under an acidic condition is a finding that has been clarified in the present invention for the first time. In other words, as another embodiment of the present invention, there is also provided a method for preparing a solid phase to which at least one selected from the group consisting of an anti-CD3 antibody, an anti-CD28 antibody, fibronectin and a fragment thereof is immobilized, characterized in that the solid phase is contacted with at least one selected from the group consisting of an anti-CD3 antibody, an anti-CD28 antibody, fibronectin and a fragment thereof under an acidic condition. Here, an acidic condition is exemplified by a pH of preferably from 1 to 6.5, and more preferably from 4 to 6.5. In addition, the solid phase is preferably exemplified by the above-mentioned cell culture carrier and the like, and these carriers can be used regardless of the materials and the presence or absence of surface treatment.

In addition, regarding the immobilization of the fibronectin fragment to the solid phase, the immobilization can be also carried out in accordance with the methods described in WO 97/18318 and WO 00/09168.

Once various components mentioned above or the effective ingredients of the present invention is immobilized to the solid phase, the lymphocytes can be easily separated from the effective ingredients or the like after the lymphocytes are obtained by the method of the present invention only by separating the lymphocytes from the solid phase, so that the contamination of the effective ingredients or the like into the lymphocytes can be prevented.

Furthermore, there may be used together with the above-mentioned components a compound selected from the group consisting of acidic polysaccharides, acidic oligosaccharides, acidic monosaccharides and salts thereof which are effective for culture of cytotoxic T cells having an antigen-specific cytotoxic activity, described in WO 02/14481, or a substance selected from the following (A) to (D) described in WO 03/016511:

(A) a substance having a binding activity to CD44;
(B) a substance capable of regulating a signal emitted by binding of a CD44 ligand to CD44;
(C) a substance capable of inhibiting binding of a growth factor to a growth factor receptor; and
(D) a substance capable of regulating a signal emitted by binding of a growth factor to a growth factor receptor.

The above-mentioned substance having a binding activity to CD44 is exemplified by, for example, a CD44 ligand and/or an anti-CD44 antibody. The substance capable of regulating a signal emitted by binding of a CD44 ligand to CD44 includes, for example, various inhibitors or activators for kinase and phosphatase. The substance capable of inhibiting binding of a growth factor to a growth factor receptor includes, for example, a substance having a binding activity to a growth factor and forming a complex with the growth factor, thereby inhibiting the binding of the growth factor to a growth factor receptor, or a substance having a binding activity to a growth factor receptor, thereby inhibiting the binding of the growth factor to a growth factor receptor. Furthermore, the substance capable of regulating a signal emitted by binding of a growth factor to a growth factor receptor includes, for example, various inhibitors or activators for kinase and phosphatase. The concentration of these components in the medium is not particularly limited, so long as the desired effects can be obtained. Also, these components may be used by immobilization to the appropriate solid phase as mentioned above in addition to the coexistence of these components by dissolving the components in the medium. Here, each of various substances mentioned above can be used alone or in admixture of two or more kinds.

In the present invention, the above-mentioned components described in WO 02/14481 and WO 03/016511 can be present in a state that the components can exhibit their functions when the expansion of lymphocytes is carried out, and an existing manner of the components is not particularly limited. For example, the effective ingredients are dissolved in the medium to be used or immobilized to an appropriate solid phase, and used. The amount of the above-mentioned component contained in the culture solution is not particularly limited, so long as the desired effects are obtained. For example, the above-mentioned component is contained in an amount of preferably from 0.0001 to 10000 µg/mL, more preferably from 0.001 to 10000 µg/mL, even more preferably 0.005 to 5000 µg/mL, and even more preferably from 0.01 to 1000 µg/mL.

In addition, the lymphocytes cultured by the method of the present invention are cloned, whereby the lymphocytes can be also maintained as stable lymphocytes. In addition, by using the lymphocytes obtained by the method of the present invention, and further according to the method of the present invention and a known method, lymphocytes can be also obtained by further expanding the lymphocytes.

The lymphocytes population obtained by the method of the present invention contains lymphocytes having a cytotoxic activity, and has an ability to recognize a desired target cell. For example, the lymphocytes population destroys the cell which is to be the target by its cytotoxic activity. The cytotoxic activity of the cytotoxic lymphocytes can be assessed by a known method. For example, the cytotoxic activity of the cytotoxic lymphocytes to a target cell labeled with a radioactive substance, a fluorescent substance or the like can be assessed by determining radioactivity or fluorescence intensity from the target cell destroyed by the cytotoxic lymphocytes. The cytotoxic activity can also be detected by determining the amount of cytokine such as GM-CSF or IFN-γ specifically released from cytotoxic lymphocytes or the target cell. In addition, the cytotoxic activity can also be directly confirmed by use of an antigenic peptide-MHC complex labeled with a fluorescent dye and the like. In this case, the cytotoxic activity of the cytotoxic lymphocytes can be assessed, for example, by contacting cytotoxic lymphocytes with a first fluorescent marker coupled with a cytotoxic lymphocyte-specific antibody, followed by contacting with an antigenic peptide-MHC complex coupled with a second fluorescent marker, and analyzing the presence of double-labeled cell with flow cytometry.

Further, as described in WO 03/080817, the present inventors have found that the culture can be initiated at a low number of cells by carrying out the preparation of lymphocytes in the presence of fibronectin, a fragment thereof or a mixture thereof. In other words, also in the preparation method of the present invention, even when initiated with a small amount of cells, the cells can be cultured with a high expansion fold regardless of the size of a cell culture equipment. According to the method of the present invention, the expansion of the lymphocytes can be satisfactorily carried out by culture procedures using one cell culture equipment, i.e., one culture system. Therefore, according to the method of the present invention, a method for preparing lymphocytes which does not require the step of diluting the cell culture solution can be accomplished.

For example, when the expansion of the lymphocytes of the present invention is initiated at a low number of cells in a cell culture equipment, the expansion can be carried out by using an amount of the cells satisfying the conditions selected from the following (X) and (Y) at a low concentration or low density at the initiation of culture:

(X) a ratio of the amount of cells to the culture area in the cell culture equipment to be used being preferably from 1 cell/cm$^2$ to 5×10$^5$ cells/cm$^2$, more preferably from 10 cells/cm$^2$ to 1×10$^5$ cells/cm$^2$, even more preferably from 1×10$^2$ cells/cm$^2$ to 5×10$^4$ cells/cm$^2$; and
(Y) a concentration of the cells in the medium being preferably from 1 cell/mL to 5×10$^5$ cells/mL, more preferably from 10 cells/mL to 1×10$^5$ cells/mL, and even more preferably from 1×10$^2$ cells/mL to 5×10$^4$ cells/mL.

The amount of cells as used herein refers to the number of cells to be used for the culture.

In addition, in the method of the present invention, there is exemplified a method comprising the step of carrying out the expansion of the lymphocytes in one culture system, which does not require the step of dilution procedure of the cell culture solution.

In addition, the method of the present invention is also useful for cloning of CTLs since the method is also suitable for expansion from a small amount of lymphocytes. In other words, also upon proliferating a selected small number of cells of CTLs, the method of the present invention can be preferably used.

Furthermore, as described in WO 2005/019450, the present inventors have found that the culture can also be carried out at a large number of cells by carrying out the preparation of lymphocytes in the presence of fibronectin, a fragment thereof or a mixture thereof. In other words, in the case where a method for preparing lymphocytes in a cell culture equipment including at least one time of step of diluting the cell culture solution with a fresh medium, step of exchanging the medium, or step of exchanging the cell culture equipment during the culture, even when the concentration of the cells in the cell culture solution immediately after these steps are set to be at a high concentration (for example, the concentration of the cells in the cell culture solution being from $2 \times 10^5$ cells/mL to $1 \times 10^8$ cells/mL, preferably from $2 \times 10^5$ cells/mL to $5 \times 10^7$ cells/mL, more preferably from $2 \times 10^5$ cells/mL to $2 \times 10^7$ cells/mL) or the ratio of the number of the cells in the cell culture solution to the culture area in the cell culture equipment immediately after these steps are set to be at a high density (for example, the ratio of the number of the cells in the cell culture solution to the culture area in the cell culture equipment being from $1 \times 10^5$ cells/cm$^2$ to $1 \times 10^8$ cells/cm$^2$, preferably from $1 \times 10^5$ cells/cm$^2$ to $5 \times 10^7$ cells/cm$^2$, more preferably from $1 \times 10^5$ cells/cm$^2$ to $2 \times 10^7$ cells/cm$^2$), a good expansion fold can be accomplished. The culture at a large number of cells of the present invention refers to preparation of lymphocytes of which conditions are set to be at a high concentration or at a high density, wherein the concentration of the cells in the cell culture solution is from $2 \times 10^5$ cells/mL to $1 \times 10^8$ cells/mL, or the ratio of the number of the cells in the cell culture solution to the culture area in the cell culture equipment is from $1 \times 10^5$ cells/cm$^2$ to $1 \times 10^8$ cells/cm$^2$, upon setting the cell concentration or cell density during the culture. Here, as used herein, the expression "immediately after the step of diluting the cell culture solution with a fresh medium, immediately after the step of exchanging the medium, or immediately after the step of exchanging the cell culture equipment" does not comprise the initiation of the culture.

In addition, in the method of the present invention, especially in expansion of CTLs, the cells can be co-cultured with appropriate feeder cells. When the lymphocytes are co-cultured with the feeder cells, it is desired that the medium is one that is suitable for maintenance and growth of both the lymphocytes and the feeder cells. As the medium, a commercially available medium can be used.

The feeder cells used for the method of the present invention are not particularly limited, so long as the feeder cells stimulate lymphocytes cooperatively with an anti-CD3 antibody and an anti-CD28 antibody to activate T cell receptor. In the present invention, for example, PBMCs or B cells transformed with Epstein-Barr virus (EBV-B cells) are used. Usually, feeder cells are used after their proliferating ability is taken away by means of irradiation or the like. Incidentally, the amount of the feeder cells contained in the medium may be determined according to the known method. For example, the feeder cells are contained in an amount of preferably from $1 \times 10^5$ cells/mL to $1 \times 10^7$ cells/mL.

In a particularly preferred embodiment, non-virus-infected cells, for example, cells other than EBV-B cells, are used as feeder cells. By using the non-virus-infected cells, the possibility that EBV-B cells are admixed in expanded lymphocytes can be eliminated, thereby making it possible to increase the safety in medical treatments utilizing cytotoxic lymphocytes, such as adoptive immunotherapy.

When lymphokine-activated cells are prepared by the preparation method of the present invention, the preparation of lymphokine-activated cells is carried out by incubating peripheral blood mononuclear cells (PBMCs), NK cells, umbilical cord blood mononuclear cells, hemopoietic stem cells, blood components containing these cells, or the like, together with IL-2 in the presence of (a) fibronectin, a fragment thereof or a mixture thereof, (b) a CD3 ligand, and (c) a CD28 ligand.

In addition, the general conditions for culturing lymphokine-activated cells may be set in accordance with the known conditions [for example, see *Saibo Kogaku* (*Cell Technology*), 14(2), 223-227, (1995); *Saibo Baiyo* (*Cell Culture*) 17(6), 192-195, (1991); *THE LANCET*, 356, 802-807, (2000); *Current Protocols in Immunology*, supplement 17, UNIT 7.7], except that the above-mentioned medium is used. The culture conditions are not particularly limited, and the conditions which are used in ordinary cell culture can be employed. For example, the culture can be carried out under the conditions of 37° C. in the presence of 5% $CO_2$, and the like. This culture is usually carried out for about 2 to about 15 days. In addition, the step of diluting the cell culture solution, the step of exchanging the medium, or the step of exchanging the cell culture equipment can be carried out at appropriate intervals.

The cells are cultured in the same manner as in the above-mentioned expansion of the lymphokine-activated cells in the presence of (a) fibronectin, a fragment thereof or a mixture thereof, (b) a CD3 ligand, and (c) a CD28 ligand, whereby, a high expansion fold can be accomplished also in expansion of CTLs and TILs. In the present invention, there is no particular limitation in the expansion of these cells except that these cells are cultured in the presence of (a) fibronectin, a fragment thereof or a mixture thereof, (b) a CD3 ligand, and (c) a CD28 ligand. The procedures can be carried out using a medium appropriate for culture of the above-mentioned cells. As to the amount of (a) fibronectin, a fragment thereof or a mixture thereof, (b) a CD3 ligand, and (c) a CD28 ligand used, the method of adding the components and the like, appropriate ones may be selected in accordance with the above-mentioned method.

Incidentally, as described in Example 3, lymphocytes obtained by the preparation method of the present invention have the feature that the amount of IL-2 production is very large. IL-2 production from lymphocytes is known to be an index of lymphocyte activation, as also described in Zhou X. Y. et al., The journal of immunology, 168, 3847-3854, (2002). For example, when a co-stimulation with an anti-CD3 antibody and an anti-CD28 antibody is carried out in expansion of lymphocytes, it is known that the amount of IL-2 production is high as compared to the case where a stimulation only with an anti-CD3 antibody is carried out. In other words, since the lymphocytes obtained by the preparation method of the present invention are very high in the amount of IL-2 production, it can be said that the lymphocytes are activated lymphocytes and are lymphocytes suitable for use in adoptive immunotherapy.

Diseases to which the lymphocytes prepared by the method of the present invention are administered are not particularly limited, and are exemplified by, for example, cancer, malignant tumor, hepatitis, and infectious diseases caused by a virus such as influenza or HIV, a bacteria, or a fungus, for example, tuberculosis, MRSA, VRE, and deep-seated mycosis. In addition, when a foreign gene is further introduced thereto as described below, the effects can be also expected for various genetic diseases. The lymphocytes prepared by the method of the present invention can also be utilized for donor lymphocyte infusion and the like for the purpose of prevention from an infectious disease after bone marrow transplantation or X-ray irradiation.

In another embodiment of the present invention, there is provided a medium for culturing lymphocytes, comprising (a) fibronectin, a fragment thereof or a mixture thereof, (b) a CD3 ligand, and (c) a CD28 ligand, as effective ingredients. The medium further comprises other optional component, for example, a medium component, a protein, and cytokines (preferably IL-2), which are used for a known cell culture, and other desired components. The amount of the effective ingredients of the present invention and the like contained in the medium is not particularly limited, so long as the desired effects of the present invention can be obtained. The amount contained can be appropriately determined as desired, for example, in accordance with the amount of the effective ingredients and the like contained in the above-mentioned medium used in the method of the present invention. One embodiment of the medium of the present invention encompasses a medium containing a cell culture carrier to which (a) fibronectin, a fragment thereof or a mixture thereof, (b) a CD3 ligand, and (c) a CD28 ligand are immobilized and a medium provided being included in the cell culture equipment to which (a) fibronectin, a fragment thereof or a mixture thereof, (b) a CD3 ligand, and (c) a CD28 ligand are immobilized.

Further, the present invention provides lymphocytes obtained by the method for preparing lymphocytes of the present invention mentioned above. In addition, the present invention provides a medicament (therapeutic agent) comprising the lymphocytes as an effective ingredient. Especially, the above-mentioned therapeutic agent comprising the lymphocytes is suitably used in adoptive immunotherapy. In the adoptive immunotherapy, the lymphocytes suitable for treating a patient are administered to the patient by, for example, intravenous administration. The therapeutic agent is very useful for use in the above-mentioned diseases and donor lymphocyte infusion. The therapeutic agent can be prepared by, for example, blending the lymphocytes prepared by the method of the present invention as an effective ingredient with, for example, a known organic or inorganic carrier suitable for non-oral administration, an excipient, a stabilizing agent and the like, according to a method known in the pharmaceutical field. Incidentally, the amount of lymphocytes of the present invention contained in the therapeutic agent, the dose of the therapeutic agent, and various conditions for the therapeutic agent can be appropriately determined according to the known adoptive immunotherapy.

The method for preparing lymphocytes of the present invention can further comprise the step of transducing a foreign gene into the lymphocytes. In other words, one embodiment of the present invention provides a method for preparing lymphocytes, further comprising the step of transducing a foreign gene into lymphocytes. Here, the term "foreign" refers to those which are foreign to lymphocytes into which a gene is to be transduced.

By carrying out the method for expanding the lymphocytes of the present invention, the ability for proliferation of the cultured lymphocytes is enhanced. Therefore, by combining the method for preparing lymphocytes of the present invention with the step of transducing a gene, increase in the gene-transducing efficiency is expected.

A means for transducing a foreign gene is not particularly limited, and an appropriate method can be selected from a known method for transducing a gene to be used. The step of transducing a gene can be carried out at any given point during the preparation of lymphocytes. For example, it is preferable to carry out the step simultaneously with the above-mentioned expansion of the lymphocytes or after the step, from the viewpoint of working efficiency.

As the above-mentioned method for transducing a gene, any of methods using a viral vector, and methods without using the vector can be employed in the present invention. The details of those methods have been already published in numerous literatures.

The above-mentioned viral vector is not particularly limited, and a known viral vector ordinarily used in the method for transducing a gene, for example, retroviral vector, lentiviral vector, adenoviral vector, adeno-associated viral vector, simian viral vector, vaccinia viral vector, sendai viral vector, or the like is used. Especially preferably, as the viral vector, retroviral vector, adenoviral vector, adeno-associated viral vector, lentiviral vector, or simian viral vector is used. As the above-mentioned viral vector, those lacking replication ability so that the viral vector cannot self-replicate in an infected cell are preferable.

The retroviral vector and lentiviral vector are used for the purpose of gene therapy or the like because there can be stably incorporated a foreign gene inserted into the vectors in chromosomal DNA in the cell into which the vectors are to be transduced. Since the vectors have a high infection efficiency to the cell during mitosis and proliferation, the gene transduction is preferably carried out in the expansion step in the present invention.

As the method for transducing a gene without using a viral vector, for example, a method using a carrier such as liposome or ligand-polylysine, calcium phosphate method, electroporation method, particle gun method or the like can be used, and does not limit the present invention. In this case, there is transduced a foreign gene incorporated into plasmid DNA or linear DNA.

The foreign gene to be transduced into lymphocytes in the present invention is not particularly limited, and an arbitrary gene which is desired to be transduced into the above-mentioned cells can be selected. As the gene as described above, besides a gene encoding a protein (for example, an enzyme, cytokines, receptors or the like), for example, a gene encoding an antisense nucleic acid, siRNA (small interfering RNA) or a ribozyme can be used. In addition, an appropriate marker gene which is capable of selecting cells into which a gene is transduced may be simultaneously transduced.

The above-mentioned foreign gene can be, for example, inserted into a vector, a plasmid or the like, so that the foreign gene is expressed under the control of an appropriate promoter, and used. In addition, in order to achieve an efficient transcription of a gene, there may exist in a vector other regulating element which cooperates with a promoter or a transcription initiation site, for example, an enhancer sequence or a terminator sequence. In addition, for the purpose of inserting a foreign gene into a chromosome of lymphocytes in which the gene is transduced by homologous recombination, for example, a foreign gene may be arranged between flanking sequences comprising nucleotide sequences each having homology to nucleotide sequences located on both sides of the desired target insertion site of the gene in the chromosome. The foreign gene to be transduced may be one that is a naturally occurring or an artificially generated, or may be one in which DNA molecules having different origins from each other are bound by a known means such as ligation. Moreover, the foreign gene may be one having a sequence in which a mutation is introduced into a naturally occurring sequence depending upon its purpose.

According to the method of the present invention, for example, a gene encoding an enzyme associated with the resistance to a drug used for the treatment of a patient with cancer or the like can be transduced into lymphocytes, thereby giving the lymphocytes a drug resistance. If the lymphocytes as described above are used, adoptive immunotherapy and drug therapy can be combined, and, therefore, higher therapeutic effects can be obtained. The drug resistance gene is exemplified by, for example, a multidrug resistance gene.

On the other hand, conversely to the above-mentioned embodiment, a gene so as to give sensitivity to a particular drug can be transduced into lymphocytes, thereby giving sensitivity to the drug. In this case, the lymphocytes after being transplanted to a living body can be removed by administering the drug. The gene for giving sensitivity to a drug is exemplified by, for example, a thymidine kinase gene.

EXAMPLES

The present invention will be more concretely described by means of Examples, without intending to limit the scope of the present invention thereto in any way.

Example 1

Determination of Expansion Fold in Lymphocytes Expansion by Co-Stimulation with CH-296, Anti-Human CD3 Antibody, and Anti-Human CD28 Antibody (1) Isolation and Storage of PBMCs Blood component was collected from a human normal individual donor, obtained with informed consent. Thereafter, the collected blood was diluted 2-folds with a phosphate buffered saline, overlaid on Ficol-paque (manufactured by Amersham Biosciences), and centrifuged at 500×g for 20 minutes. The peripheral blood mononuclear cells (PBMCs) in the intermediate layer were collected with a pipette, and washed. The collected PBMCs were suspended in a storage solution of 90% FBS (manufactured by Cambrex Corporation)/10% DMSO (manufactured by SIGMA), and stored in liquid nitrogen. During lymphocytes expansion, these stored PBMCs were rapidly melted in water bath at 37° C., and washed with RPMI 1640 medium (manufactured by SIGMA) containing 10 μg/mL DNase (manufactured by Calbiochem). Thereafter, the number of living cells was calculated by trypan blue staining method. The cells were subjected to each experiment.

(2) Immobilization of Anti-Human CD3 Antibody, Anti-Human CD28 Antibody and CH-296 to Plate The amount 1.9 mL each of an aqueous acetate buffer solution containing an anti-human CD3 antibody (manufactured by Janssen-Kyowa Co., Ltd.) at a final concentration of 5 μg/mL was added to a 12-well cell culture plate (manufactured by Becton Dickinson). The aqueous acetate buffer solution was prepared by mixing 0.2 M acetic acid (prepared from 00212-43, manufactured by NACALAI TESQUE, Inc.) and 0.2 M aqueous sodium acetate solution (prepared from 311-19, manufactured by NACALAI TESQUE, Inc.) at a ratio of 1:4 (volume ratio), so as to have a pH of 5.3. Upon the addition, to a group to be carried out a stimulation with an anti-human CD28 antibody was added an anti-human CD28 antibody (manufactured by DakoCytomation, RB342) so as to have a final concentration of 5 μg/mL, and to a group to be carried out a stimulation with CH-296 was added CH-296 so as to have a final concentration of 25 μg/mL. These plates were incubated at room temperature for 5 hours, and thereafter the aqueous acetate buffer solution containing the antibody and the CH-296 was removed by aspiration. Each well was washed twice with a phosphate buffered saline and then once with RPMI medium, and was subjected to each experiment.

(3) Expansion of Lymphocytes

PBMCs which were prepared in item (1) of Example 1 were suspended in AIM-V (manufactured by Invitrogen Corporation) containing 3% human AB serum (manufactured by Cambrex Corporation) (hereinafter abbreviated as 3% AIM-V) so as to have a concentration of $0.5 \times 10^6$ cells/mL to adjust a cell suspension. Thereafter, 3% AIM-V was put on plates immobilized with the antibody and the CH-296 which were prepared in item (2) of Example 1, in a volume of 2 mL/well, and the adjusted cell suspension was added thereto in a volume of 1 mL/well each. Thereafter, IL-2 (manufactured by Shionogi & Co., Ltd.) was added to a group stimulated only with the anti-human CD3 antibody and a group co-stimulated with the anti-human CD3 antibody and the CH-296, so as to have a final concentration of 1000 U/mL (in other words, IL-2 was not added to a group in which the stimulation was carried out using the anti-human CD28 antibody), and these plates were subjected to culture at 37° C. in 5% $CO_2$ (zeroth day of culture). As to each group, on the fourth day, the seventh day, and the eleventh day from the initiation of culture, the subculture procedures were carried out by the following method. A part of the cell culture solution was collected, and the number of living cells was counted by trypan blue staining method. Thereafter, a culture solution diluted to a proper concentration with AIM-V containing 1% human AB serum was transferred to a fresh 12.5 $cm^2$ flask (manufactured by Becton Dickinson, 353107) to which nothing was immobilized, and IL-2 was added thereto so as to have a final concentration of 500 U/mL, so that the culture solution was subjected to subculture (IL-2 was added to all groups on the fourth day from the initiation of culture or after). Here, the dilution was carried out so as to have a cell concentration after the subculture procedures of $0.05 \times 10^6$ cells/mL on the fourth day, $0.15 \times 10^6$ cells/mL on the seventh day, and $0.2 \times 10^6$ cells/mL on the eleventh day, from the initiation of culture, respectively. On the fifteenth day from the initiation of culture, the number of living cells was counted by trypan blue staining method, and an expansion fold was calculated by comparing the number of the cells with the number at the initiation of culture. The results are shown in Table 1. Table 1 shows proliferation ratios of cell group each stimulated with only the anti-human CD3 antibody, with the anti-human CD3 antibody and the CH-296, with the anti-human CD3 antibody and the anti-human CD28 antibody, and with the anti-human CD3 antibody, the anti-human CD28 antibody, and the CH-296.

TABLE 1

| Stimulation Conditions | Expansion Fold (folds) |
|---|---|
| Anti-CD3 Antibody | 278 |
| Anti-CD3 Antibody + CH-296 | 2331 |
| Anti-CD3 Antibody + Anti-CD28 Antibody | 1486 |
| Anti-CD3 Antibody + Anti-CD28 Antibody + CH-296 | 4170 |

It has been generally known that a proliferation of lymphocytes is accelerated by simultaneous stimulation with the anti-human CD3 antibody and the anti-human CD28 antibody. As shown in Table 1, co-stimulation with the anti-human CD3 antibody and the CH-296 showed an even higher expansion fold, and it was clarified that an expansion fold was more elevated by further adding stimulation with the CH-296 to co-stimulation with the anti-human CD3 antibody and the anti-human CD28 antibody.

Example 2

Immobilization Efficiency of Anti-Human CD3 Antibody, Anti-Human CD28 Antibody and CH-296 on Plate at Various pH As buffer solutions, a phosphate buffered saline at a pH of 7.4 from Dulbecco's PBS powder (manufactured by NISSUI PHARMACEUTICAL Co., Ltd.), an aqueous sodium phosphate buffer solution at a pH of 6.2 by mixing 0.2 M aqueous sodium dihydrogen phosphate solution (prepared from 317-20, manufactured by NACALAI TESQUE, Inc.) and 0.2 M aqueous di-sodium hydrogen phosphate solution (prepared from 318-01, manufactured by NACALAI TESQUE, Inc.,) at a ratio of 8.15:1.85 (volume ratio), and an aqueous acetate buffer solution at a pH of 5.3 by mixing 0.2 M acetic acid and 0.2 M aqueous sodium acetate solution at a ratio of 1:4 (volume ratio) were respectively prepared. The amount 100 μl each of each solution of an anti-human CD28 antibody adjusted to a final concentration of 5 μg/mL using these buffer solutions was added to each well of a 96-well cell culture plate (manufactured by Becton Dickinson, 353072). Thereafter, these plates were incubated at room temperature for 5 hours, and immobilizations at various pH were carried out. Similarly, 160 μl each of each solution of an anti-human CD3 antibody adjusted to a final concentration of 5 μg/mL or each solution of CH-296 adjusted to a final concentration of 25 μg/mL was added to each well, and immobilizations were similarly carried out at room temperature for 5 hours. After the termination of these immobilizations, the buffer solution containing the antibody or the CH-296 was removed, and 300 μl each of Block Ace (manufactured by Dainippon Pharmaceutical, UK-B25) diluted 4-folds with a phosphate buffered saline was added thereto and allowed to stand at room temperature for 1 hour, to carry out blocking. Thereafter, the solution was removed, and an antibody for the detection which was dissolved in Block Ace diluted 10-folds with a phosphate buffered saline was added thereto in the same amount as a liquid amount of immobilization. As an antibody for the detection, HRP-rabbit Anti-Mouse IgG (manufactured by ZYMED, 61-6520) was used for the detection of the anti-human CD3 antibody and the anti-human CD28 antibody, and HRP labeled Anti-Human Fibronectin (Clone FNH3-8, manufactured by TAKARA BIO INC., M115) was used for the detection of the CH-296. After a reaction for 1 hour, the solution was again removed, and ABTS solution (prepared from A1888-2G, manufactured by SIGMA) was added thereto in the same amount as a liquid amount of immobilization. After the reaction for 10 minutes, 150 mM oxalic acid solution (manufactured by NACALAI TESQUE, Inc., prepared from 25806-74) in a half amount as the amount of ABTS added was added thereto, to terminate the reaction. Incidentally, upon removing the each solution, washing procedures with a phosphate buffered saline were carried out for 3 times. After the termination of the reaction, absorbance at 405 nm was determined with an absorbance plate reader (MicroReader 4, manufactured by Hyperion). The results are shown in Table 2. Table 2 compares immobilization efficiencies in three conditions at pH of 7.4, 6.2, and 5.3 for the anti-human CD3 antibody, the anti-human CD28 antibody, and the CH-296, by values of absorbance.

TABLE 2

|  | Absorbance | | |
| --- | --- | --- | --- |
| Antibody, CH-296 | pH of 7.4 | pH of 6.2 | pH of 5.3 |
| Anti CD3 Antibody | 1.824 | 2.799 | 3.501 |
| Anti CD28 Antibody | 0.030 | 0.353 | 1.528 |
| CH-296 | 0.501 | 0.769 | 1.046 |

As shown in Table 2, for all of the anti-human CD3 antibody, the anti-human CD28 antibody, and the CH-296, immobilization efficiency was elevated as pH was lowered, and it was clarified that immobilization efficiency was the highest upon carrying out immobilization in the condition at a pH of 5.3.

Example 3

Comparison of Amount of IL-2 Production Upon Carrying Out Expansion of Lymphocytes Using Plate Immobilized at Various pH Lymphocytes were expanded in the same manner as in Example 1, provided that, as to immobilization of the anti-human CD3 antibody, the anti-human CD28 antibody, and the CH-296 on a 12-well cell culture plate, there were used a phosphate buffered saline at a pH of 7.4 and an aqueous sodium phosphate buffer solution at a pH of 6.2, not the aqueous acetate buffer solution at a pH of 5.3, as buffer solutions. Both buffer solutions were prepared in the same manner as in Example 2. In addition, the number of cells planted at the initiation of culture was 1×10$^6$ cells per 1 well. Until the fourth day from the initiation of culture, the culture supernatant was collected about every 24 hours, and subjected to ELISA analysis, and a concentration of IL-2 in the supernatant was determined. ELISA analysis was carried out using ELISA Development Kit human IL-2 (manufactured by Genzyme/Techne, 4904). The results are shown in Table 3. Table 3 compares the amounts of IL-2 production upon stimulating cells with the anti-human CD3 antibody, the anti-human CD28 antibody, and the CH-296, in a case being immobilized using the phosphate buffered saline at a pH of 7.4 and a case being immobilized using the aqueous sodium phosphate buffer solution at a pH of 6.2.

TABLE 3

|  |  | Concentration of IL-2 (U/mL) Days from Initiation of Culture | | | |
| --- | --- | --- | --- | --- | --- |
| pH | Stimulation Conditions | First Day | Second Day | Third Day | Fourth Day |
| 7.4 | Anti-CD3 Antibody + Anti-CD28 Antibody | 1 | 14 | 5 | 0 |
|  | Anti-CD3 Antibody + Anti-CD28 Antibody + CH-296 | 63 | 244 | 277 | 46 |

TABLE 3-continued

| | | Concentration of IL-2 (U/mL) Days from Initiation of Culture | | | |
|---|---|---|---|---|---|
| pH | Stimulation Conditions | First Day | Second Day | Third Day | Fourth Day |
| 6.2 | Anti-CD3 Antibody + Anti-CD28 Antibody | 28 | 80 | 71 | 0 |
| | Anti-CD3 Antibody + Anti-CD28 Antibody + CH-296 | 107 | 322 | 380 | 153 |

As shown in Table 3, the amount of IL-2 production was elevated when immobilization was carried out at a pH of 6.2 better than at a pH of 7.4.

Similarly, the amounts of IL-2 production in a case being immobilized using an aqueous sodium phosphate buffer solution at a pH of 6.2 and a case being immobilized using an aqueous acetate buffer solution at a pH of 5.3 were also compared. Lymphocytes were expanded in the same manner as in Example 1, provided that, as to immobilization of the anti-human CD3 antibody, the anti-human CD28 antibody, and the CH-296 to a 12-well cell culture plate, a group using the aqueous sodium phosphate buffer solution at a pH of 6.2 in addition to the aqueous acetate buffer solution at a pH of 5.3 was set as buffer solutions. Until the fourth day from the initiation of culture, the culture supernatant was collected about every 24 hours, and subjected to ELISA analysis, and a concentration of IL-2 in the supernatant was determined in the same manner as mentioned above. The results are shown in Table 4. Table 4 compares the amounts of IL-2 production upon stimulating cells with the anti-human CD3 antibody, the anti-human CD28 antibody, and the CH-296, in a case being immobilized using the aqueous sodium phosphate buffer solution at a pH of 6.2 and a case being immobilized using the aqueous acetate buffer solution at a pH of 5.3.

TABLE 4

| | | Concentration of IL-2 (U/mL) Days from Initiation of Culture | | | | Amount of IL-2 per Unit Number of Cells on Fourth |
|---|---|---|---|---|---|---|
| pH | Stimulation Conditions | First Day | Second Day | Third Day | Fourth Day | Day of Culture (U/$10^6$ cells) |
| 6.2 | Anti-CD3 Antibody + Anti-CD28 Antibody | 7 | 16 | 21 | 8 | 35 |
| | Anti-CD3 Antibody + Anti-CD28 Antibody + CH-296 | 59 | 212 | 361 | 371 | 1100 |
| 5.3 | Anti-CD3 Antibody + Anti-CD28 Antibody | 32 | 63 | 77 | 58 | 236 |
| | Anti-CD3 Antibody + Anti-CD28 Antibody + CH-296 | 146 | 514 | 843 | 937 | 2997 |

As shown in Table 4, the amount of IL-2 production is elevated when immobilization was carried out at a pH of 5.3 better than at a pH of 6.2. In addition, it was shown that the cells obtained by stimulation with the anti-human CD3 antibody, the anti-human CD28 antibody, and the CH-296 had a high ability of IL-2 production as compared to the cells obtained by stimulation with the anti-human CD3 antibody and the anti-human CD28 antibody.

It has been generally known that IL-2 production is induced by co-stimulation with an anti-human CD3 antibody and an anti-human CD28 antibody. As shown in Table 3 and Table 4, it was clarified that the amount of IL-2 production was increased by further adding stimulation with CH-296 thereto, and a new effectiveness of CH-296 was found. In addition, it was clarified that, immobilization efficiency is the highest and the amount of IL-2 production is increased by carrying out immobilizations of the anti-human CD3 antibody, the anti-human CD28 antibody, and the CH-296 to plate in the condition at a pH of 5.3. In other words, it was clarified that stimulation to cells with the antibodies and the CH-296 is more heightened by carrying out immobilization in the condition at a pH of 5.3, so that proliferation of lymphocytes, cytokine production, and the like are more activated, and it was found that the lymphocytes expansion using the CH-296 became more efficient. Here, in Table 3 and Table 4, it is considered that the difference found in the amounts of IL-2 production of cells on the fourth day of the culture in the immobilization condition at a pH of 6.2 was affected by the difference in the number of cells at the initiation of culture.

Example 4

Lymphocytes Expansion Using Beads to which Anti-Human CD3 Antibody and Anti-Human CD28 Antibody were Immobilized and Beads to which CH-296 was Immobilized (1) Preparation of Control Beads and CH-296 Beads Dynabeads M-450 Epoxy (manufactured by DYNAL, 140-01) was used to prepare beads to which CH-296 was immobilized (hereinafter referred to as CH-296 beads) and beads to which any antibody and protein were not immobilized and blocking was only carried out (hereinafter referred to as control beads). The preparation was carried out according to the protocol attached to the product. Immobilization was carried out by suspending beads into a solution of CH-296 at a final concentration of 200 μg/mL so as to have a concentration of $4\times10^8$ beads/mL and incubating at 5° C. for 18 hours. Blocking was carried out using human serum albumin (buminate 25%, manufactured by Baxter International Inc., 7783).

(2) Expansion of Lymphocytes using Beads

Dynabeads CD3/CD28 T Cell Expander (manufactured by DYNAL, 111-31, hereinafter abbreviated as T Cell Expander) was washed in accordance with the appended protocol, and thereafter suspended into AIM-V containing 1% human AB serum (hereinafter abbreviated as 1% AIM-V) so as to have a concentration of 3×10⁶ beads/mL, and added to a 12-well cell culture plate in a volume of 1 mL/well each. The control beads and the CH-296 beads which were prepared in item (1) of Example 4 were washed in the same manner as T Cell Expander, and thereafter suspended into 1% AIM-V so as to have a concentration of 1.9×10⁶ beads/mL. The control beads suspension was added to a group co-stimulated with the anti-human CD3 antibody and the anti-human CD28 antibody, and the CH-296 beads suspension was added to a group stimulated with the anti-human CD3 antibody, the anti-human CD28 antibody, and the CH-296, by way of adding to the T Cell Expander suspension in a 12-well cell culture plate in a volume of 1 mL/well each. PBMCs which were prepared in item (1) of Example 1 were suspended into 1% AIM-V so as to have a concentration of 1×10⁶ cells/mL, and was added to the 12-well cell culture plate to which the beads suspension was added, in a volume of 1 mL/well each (3 mL/well, in total). Thereafter, IL-2 was added to each well so as to have a final concentration of 200 U/mL, and the plate was subjected to culture in an incubator in 5% $CO_2$ at 37° C. (zeroth day of culture). On the fourth day, the seventh day, and the tenth day from the initiation of culture, the subculture procedures were carried out by the following method. A part of the cell culture solution was collected, the number of living cells was counted by trypan blue staining method, a culture solution was diluted to a proper concentration with 1% AIM-V and was transferred to a 12.5 cm² flask, and IL-2 was added thereto so as to have a final concentration of 200 U/mL. The dilution of the culture solution was carried out so as to have a cell concentration after the subculture procedures of 0.05×10⁶ cells/mL on the fourth day, 0.1×10⁶ cells/mL on the seventh day, and 0.15×10⁶ cells/mL on the tenth day, respectively. On the fourteenth day from the initiation of culture, the number of living cells was counted, and an expansion fold was calculated by comparing the number of the cells with the number at the initiation of culture. The results are shown in Table 5. Table 5 shows proliferation ratios after the expansion for fourteen days, as to the cell groups stimulated with T Cell Expander and the control beads or T Cell Expander and the CH-296 beads.

TABLE 5

| Stimulation Conditions | Expansion Fold (folds) |
|---|---|
| T Cell Expander + Control Beads | 377 |
| T Cell Expander + CH296 Beads | 809 |

As shown in Table 5, a group to which the CH-296 beads were added showed a higher proliferation ratio than a group to which the control beads were added. It was clarified that proliferation of lymphocytes could be further accelerated by simultaneous addition of the beads to which the CH-296 was immobilized, in addition to the beads to which the anti-human CD3 antibody and the anti-human CD28 antibody were immobilized.

Example 5

Lymphocytes Expansion Using Beads to which Anti-Human CD3 Antibody, Anti-Human CD28 Antibody, and CH-296 were Immobilized (1) Preparation of Beads to which Anti-Human CD3 Antibody, Anti-Human CD28 Antibody, and CH-296 were Immobilized Preparation was carried out in the same manner as in item (1) of Example 4, provided that, immobilization was carried out using a buffer solution in admixture of an anti-human CD3 antibody at a final concentration of 25 µg/mL, an anti-human CD28 antibody at a final concentration of 50 µg/mL, and CH-296 at a final concentration of 125 µg/mL.

(2) Expansion of Lymphocytes Using Beads

Expansion was carried out in the same manner as in item (2) of Example 4, provided that, at the initiation of culture, beads which were prepared in item (1) of Example 5 was used as beads to stimulate cells, and GT-T503 medium containing 0.5% human AB serum and 0.2% human serum albumin (manufactured by TAKARA BIO INC., hereinafter abbreviated as 0.5% GT-T503) was used as a medium. The number of cells was 0.5×10⁶ cells/well, and the amount of the culture solution was 1.5 mL/well. There were set a group in which amount of the beads added was 0.5×10⁶ beads/well and a group in which amount of the beads added was 5×10⁶ beads/well. In addition, as to the subculture, the subculture procedures were carried out on the fourth day, the eighth day, and the eleventh day from the initiation of culture, so as to have a cell concentration after the subculture of 0.02×10⁶ cells/mL on the fourth day, 0.15×10⁶ cells/mL on the eighth day, and 0.3×10⁶ cells/mL on the eleventh day, respectively. As a medium, 0.5% GT-T503 was used. On the fourteenth day from the initiation of culture, the number of living cells was counted, and an expansion fold was calculated by comparing the number of the cells with the number at the initiation of culture. The results are shown in Table 6. Table 6 shows proliferation ratios after the expansion for fourteen days of a cell group stimulated with 0.5×10⁶ beads and a cell group stimulated with 5×10⁶ beads, as to the cells stimulated with the beads to which the anti-human CD3 antibody, the anti-human CD28 antibody, and the CH-296 were immobilized.

TABLE 6

| Stimulation Conditions | Expansion Fold (folds) |
|---|---|
| 0.5 × 10⁶ beads | 424 |
| 5 × 10⁶ beads | 625 |

As shown in Table 6, it was shown that the expansion of lymphocytes could be carried out by using beads to which the anti-human CD3 antibody, the anti-human CD28 antibody, and the CH-296 were simultaneously immobilized.

INDUSTRIAL APPLICABILITY

According to the present invention, there is provided a method for preparing lymphocytes. The method has a high proliferation ratio of the cells, and the lymphocytes obtained by the present invention are suitably used, for example, in adoptive immunotherapy. Therefore, there is expected a great contribution of the method of the present invention to the medical field.

BRIEF DESCRIPTION OF THE DRAWINGS

FIG. 1 A schematic view showing a domain structure of fibronectin.

SEQUENCE LISTING FREE TEXT

SEQ ID NO: 1; Partial region of fibronectin named III-8.
SEQ ID NO: 2; Partial region of fibronectin named III-9.
SEQ ID NO: 3; Partial region of fibronectin named III-10.
SEQ ID NO: 4; Partial region of fibronectin named III-11.
SEQ ID NO: 5; Partial region of fibronectin named III-12.
SEQ ID NO: 6; Partial region of fibronectin named III-13.
SEQ ID NO: 7; Partial region of fibronectin named III-14.

SEQ ID NO: 8; Partial region of fibronectin named CS-1.
SEQ ID NO: 9; Fibronectin fragment named C-274.
SEQ ID NO: 10; Fibronectin fragment named H-271.
SEQ ID NO: 11; Fibronectin fragment named H-296.
SEQ ID NO: 12; Fibronectin fragment named CH-271.
SEQ ID NO: 13; Fibronectin fragment named CH-296.
SEQ ID NO: 14; Fibronectin fragment named C-CS1.
SEQ ID NO: 15; Fibronectin fragment named CHV-89.
SEQ ID NO: 16; Fibronectin fragment named CHV-90.
SEQ ID NO: 17; Fibronectin fragment named CHV-92.
SEQ ID NO: 18; Fibronectin fragment named CHV-179.
SEQ ID NO: 19; Fibronectin fragment named CHV-181.
SEQ ID NO: 20; Fibronectin fragment named H-275-Cys.
SEQ ID NO: 21; Fibronectin fragment named CH-296Na.

The invention claimed is:

1. A method for preparing lymphocytes suitable for adoptive immunotherapy comprising the step of carrying out expansion in the simultaneous presence of (a) fibronectin, a fragment thereof or a mixture thereof, (b) an immobilized CD3 ligand, and (c) an immobilized CD28 ligand.

2. The method according to claim 1, wherein the CD3 ligand is an anti-CD3 antibody.

3. The method according to claim 1, wherein the CD28 ligand is an anti-CD28 antibody.

4. The method according to claim 1, wherein the fibronectin fragment is a polypeptide (m) comprising at least any one of the amino acid sequences shown in SEQ ID NOs: 1 to 8 of Sequence Listing, or a polypeptide (n) comprising at least one amino acid sequence having substitution, deletion, insertion or addition of one or plural number of amino acids in any one of said amino acid sequences, wherein the polypeptide (n) has a function equivalent to said polypeptide (m).

5. The method according to claim 4, wherein the fibronectin fragment has a cell adhesion activity and/or a heparin binding activity.

6. The method according to claim 5, wherein the fibronectin fragment is at least one polypeptide selected from the group consisting of polypeptides having any one of the amino acid sequences shown in SEQ ID NOs: 9 to 21 of Sequence Listing.

7. The method according to claim 1, wherein the lymphocytes are lymphokine-activated cells.

8. The method according to claim 1, further comprising the step of transducing a foreign gene into lymphocytes.

9. The method according to claim 8, wherein the foreign gene is transduced using retrovirus, adenovirus, adeno-associated virus, lentivirus or simian virus.

10. A method for preparing a solid phase comprising:
contacting the solid phase with (a) fibronectin, a fragment thereof or a mixture thereof, (b) a CD3 ligand and (c) a CD28 ligand under an acidic condition.

11. The method according to claim 10, wherein the solid phase is a cell culture carrier.

12. A solid phase to which (a) fibronectin, a fragment thereof or a mixture thereof, (b) a CD3 ligand, and (c) a CD28 ligand are immobilized.

13. The solid phase according to claim 12, wherein the solid phase is a cell culture plate, a petri dish, a flask, a bag, beads, a membrane or a slide glass.

* * * * *